United States Patent
Manimaran et al.

(10) Patent No.: US 6,218,584 B1
(45) Date of Patent: Apr. 17, 2001

(54) PROCESS FOR THE PREPARATION OF TETRABROMOBISPHENOL-A

(75) Inventors: Thanikavelu Manimaran; Hassan Y. Elnagar; Richard A. Holub; Alvin E. Harkins, Jr., all of Baton Rouge, LA (US); Bonnie G. McKinnie, Hegenheim (FR)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/329,374

(22) Filed: Jun. 10, 1999

Related U.S. Application Data

(63) Continuation-in-part of application No. 09/096,332, filed on Jun. 11, 1998, which is a continuation-in-part of application No. 08/945,158, filed on Oct. 21, 1997, which is a continuation-in-part of application No. 08/426,998, filed on Apr. 24, 1995, now abandoned, and a continuation-in-part of application No. 08/426,996, filed on Apr. 24, 1995, now abandoned, which is a continuation-in-part of application No. 08/398,837, filed on Mar. 6, 1995, now abandoned, said application No. 08/945,158, is a continuation-in-part of application No. 08/550,044, filed on Oct. 30, 1995, now Pat. No. 5,723,690, which is a continuation of application No. 08/426,997, filed on Apr. 24, 1995, now Pat. No. 5,527,971.

(51) Int. Cl.[7] .................................................. C07C 39/16

(52) U.S. Cl. .......................... 568/726; 568/723; 568/724; 568/725; 568/774; 568/779

(58) Field of Search .................................. 568/726, 723, 568/724, 725, 722, 774, 779

(56) References Cited

U.S. PATENT DOCUMENTS

| | | | |
|---|---|---|---|
| 2,455,652 | 12/1948 | Bralley et al. ........................ | 260/77.5 |
| 3,029,291 | 4/1962 | Dietzler ................................ | 260/619 |
| 3,143,575 | 8/1964 | Bryner et al. ........................ | 260/619 |
| 3,182,088 | 5/1965 | Hennis ................................. | 260/619 |
| 3,234,289 | 2/1966 | Hennis ................................. | 260/619 |
| 3,363,007 | 1/1968 | Majewski et al. ................... | 260/619 |
| 3,546,302 | 12/1970 | Asadorian et al. .................. | 260/619 |
| 3,868,423 | 2/1975 | Montanari et al. ............... | 260/619 A |
| 3,929,907 | 12/1975 | Janzon et al. ..................... | 260/619 R |
| 4,013,728 | 3/1977 | Brackenridge ................... | 260/619 A |
| 4,036,894 | 7/1977 | Jenker ............................. | 260/619 A |
| 4,112,242 | 9/1978 | Swietoslawski et al. ............. | 568/726 |
| 4,180,684 | 12/1979 | Kleinschmit et al. .............. | 568/726 |
| 4,282,391 | 8/1981 | Quinn et al. ......................... | 568/726 |
| 4,283,566 | 8/1981 | Mark .................................... | 568/726 |
| 4,291,177 | 9/1981 | Mark et al. .......................... | 568/726 |
| 4,302,614 | 11/1981 | Dannenberg et al. .............. | 568/641 |
| 4,451,675 | 5/1984 | Bounds ................................ | 568/726 |
| 4,628,124 | 12/1986 | McKinnie et al. .................... | 568/726 |
| 4,692,555 | 9/1987 | Shin .................................... | 568/722 |
| 4,701,568 | 10/1987 | McKinnie et al. .................... | 568/726 |
| 4,783,556 | 11/1988 | Mitchell et al. ....................... | 568/726 |
| 4,909,997 | 3/1990 | Mitchell et al. ....................... | 422/225 |

(List continued on next page.)

FOREIGN PATENT DOCUMENTS

| | | |
|---|---|---|
| 686772 | 5/1964 | (CA) . |
| 706433 | 3/1965 | (CA) . |
| 2041220 | 3/1971 | (DE) . |
| 3417027 | 11/1985 | (DE) . |
| 0367869 | 5/1990 | (EP) . |
| 0380363 | 8/1990 | (EP) . |
| 0380365 | 8/1990 | (EP) . |
| 0472395 | 2/1992 | (EP) . |
| 0572154 | 12/1993 | (EP) . |
| 0574031 | 12/1993 | (EP) . |
| 2274586 | 1/1976 | (FR) . |
| 949306 | 2/1964 | (GB) . |
| 1031500 | 6/1966 | (GB) . |
| 1316415 | 5/1973 | (GB) . |
| 2026280 | 1/1995 | (GB) . |
| 64410 | 11/1981 | (IS) . |
| 58-225034 | 12/1983 | (JP) . |
| 60-58728 | 12/1985 | (JP) . |
| 62-48641 | 3/1987 | (JP) . |

(List continued on next page.)

OTHER PUBLICATIONS

Chemical Abstracts vol. 78, 1973, p. 328.
Chemical Abstracts vol. 96, 1982, p. 718.
Chemical Abstracts vol. 104, 1986, p. 656.
Chemical Abstracts vol. 104, 1986, p. 716.
Islam et al., "Tetrahalogenated 4:4'—Dihydroxydiphenylalkanes, their Synthesis and some of their Reactions", Egypt J. Chem. vol. 20, No. 5, 1977, pp. 483–490.
Sadygov et al., "Oxidative Bromination of 2,2–Bis(4'–Hydroxyphenyl) Propane", Neftekhimiya, vol. 30, No. 1, 1990, pp. 109–113. (Translation attached p. 1–7).
Levenspiel Chemical Reaction Eng. (1962). Chapter 6, p. 126, 1962.
Patent Abstracts of Japan, Publication No. JP 62048641, Publication Date Mar. 3, 1987, entitled "Bromination of Bisphenol Compound".
Chemical Abstract, vol. 86, 1977, pp. 570, JP 77,05745.
CAPLUS, Abstract of JP 52,034620, 1977.
WPIDS, Abstract of JP 77/034620, 1977.
JAPIO, Abstract of JP 52,005745, 1977.

Primary Examiner—Sreeni Padmanabhan
(74) Attorney, Agent, or Firm—E. E. Spielman, Jr.

(57) ABSTRACT

This invention relates, inter alia, to a process for the production of tetrabromobisphenol-A by the bromination of bisphenol-A and/or underbrominated bisphenol-A, which process features: a water and water-miscible organic solvent reaction medium; a relatively high reaction temperature; and the presence, in the reaction medium, of both (i) excess unreacted $Br_2$ during the feed of bis-phenol-A to the reactor, and (ii) sufficient HBr to protect the tetrabromobisphenol-A produced against undesirable color formation. Tetrabromobisphenol-A precipitates from the reaction mass and is easily recovered. Product of high purity (97% or more) and very low color (APHA of 50 or less) can be produced, even when using large excesses of bromine in the reaction.

75 Claims, No Drawings

U.S. PATENT DOCUMENTS

| | | | |
|---|---|---|---|
| 4,990,321 | 2/1991 | Sato et al. | 423/486 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/226 |
| 5,059,726 | 10/1991 | Eguchi et al. | 568/726 |
| 5,068,463 | 11/1991 | Walter | 568/726 |
| 5,107,035 | 4/1992 | Hines et al. | 568/726 |
| 5,138,103 | 8/1992 | Eguchi et al. | 568/726 |
| 5,208,389 | 5/1993 | McKinnie et al. | 568/726 |
| 5,237,112 | 8/1993 | LaRose | 568/726 |
| 5,283,375 | 2/1994 | McKinnie et al. | 568/726 |
| 5,302,761 | 4/1994 | Tambayashi et al. | 568/726 |
| 5,446,212 | 8/1995 | Sanders et al. | 568/726 |
| 5,527,971 | 6/1996 | McKinnie | 568/726 |
| 5,723,690 | 3/1998 | McKinnie | 568/726 |
| 5,847,232 | 12/1998 | McKinnie | 568/726 |

FOREIGN PATENT DOCUMENTS

| | | |
|---|---|---|
| 63-316748 | 12/1988 | (JP) . |
| 2196747 | 8/1990 | (JP) . |
| 4099743 | 3/1992 | (JP) . |
| 5213804 | 8/1993 | (JP) . |
| 5229976 | 9/1993 | (JP) . |
| 9611227 | 4/1996 | (WO) . |
| 9620911 | 7/1996 | (WO) . |
| 9627576 | 9/1996 | (WO) . |
| 9633964 | 10/1996 | (WO) . |

PROCESS FOR THE PREPARATION OF TETRABROMOBISPHENOL-A

REFERENCE TO RELATED APPLICATIONS

This application is a continuation-in-part of commonly-owned U.S. application Ser. Nos. 09/096,332, filed Jun. 11, 1998, and 08/945,158, filed Oct. 21, 1997. Application Ser. No. 09/096,332 is a continuation-in-part of application Ser. No. 08/945,158, which in turn is a continuation-in-part of commonly-owned application Ser. Nos. 08/426,996 and 08/426,998 both filed Apr. 24, 1995 and both now abandoned. Application Ser. No. 08/426,998 in turn is a continuation-in-part of commonly-owned application Ser. No. 08/398,837, filed Mar. 6, 1995 and now abandoned. Application Ser. No. 08/945,158 is also a continuation-in-part of commonly-owned application Ser. No. 08/550,044, filed Oct. 30, 1995, now U.S. Pat. No. 5,723,690, issued Mar. 3, 1998, which in turn is a continuation of commonly-owned application Ser. No. 08/426,997, filed Apr. 24, 1995, now U.S. Pat. No. 5,527,971, issued Jun. 18, 1996.

OTHER COMMONLY-OWNED COPENDING APPLICATIONS

Other commonly-owned copending U.S. applications relating to preparation of tetrabromobisphenol-A include Application Nos. 09/288,195, filed Apr. 8, 1999; 09/407,314, filed Sep. 28, 1999; and 09/416,855, filed Oct. 12, 1999.

TECHNICAL FIELD

This invention relates to novel, highly efficient processes for the preparation of tetrabromobisphenol-A.

BACKGROUND

Tetrabromobisphenol-A is one of the most widely used brominated flame retardants in the world. It is used extensively to provide flame retardancy for styrenic thermoplastics and for some thermoset resins.

Processes used for producing tetrabromobisphenol-A generally fall into three categories. The first category includes processes in which substantial amounts of methyl bromide are co-produced along with the tetrabromobisphenol-A. Generally, up to 40–50 pounds of methyl bromide can be expected per 100 pounds of tetrabromobisphenol-A produced. In most cases, the processes within this first category feature reacting bisphenol-A and bromine in methanol. The ring-bromination of the bisphenol-A is a substitution reaction which generates one mole of HBr per ring-bromination site. Thus, for the production of tetrabromobisphenol-A, four moles of HBr are generated per mole of tetrabromobisphenol-A produced. The HBr in turn reacts with the methanol solvent to produce the methyl bromide co-product. After the bisphenol-A and bromine feed are finished, the reactor contents are cooked for one to two hours to complete the reaction. At the end of the reaction, water is added to the reactor contents to precipitate out the desired tetrabromobisphenol-A product.

The second category of processes features the production of tetrabromobisphenol-A without the co-production of substantial amounts of methyl bromide and without the use of oxidants to convert the HBr to $Br_2$. See for example U.S. Pat. Nos. 4,990,321; 5,008,469; 5,059,726; and 5,138,10. Generally, these processes brominate the bisphenol-A at a low temperature, e.g., 0 to 20° C., in the presence of a methanol solvent and a specified amount of water. The water and low temperature attenuate the production of methyl bromide by slowing the reaction between methanol and HBr. The amount of water used, however, is not so large as to cause precipitation of the tetrabromobisphenol-A from the reaction mass during the bromination reaction. Additional water for that purpose is added at the end of the reaction. This type of process typically uses a fairly long aging or cook period after the reactants have all been fed, and requires additional process time for the final precipitation of tetrabromobisphenol-A via the last water addition.

In the third category are those processes which feature the bromination of bisphenol-A with bromine in the presence of a solvent and, optionally, an oxidant, e.g., $H_2O_2$, $Cl_2$, etc. See for example U.S. Pat. No. 3,929,907; U.S. Pat. No. 4,180,684; U.S. Pat. No. 5,068,463 and Japanese 77/034620 B4 77/09/05. The solvent is generally a water-immiscible halogenated organic compound. Water is used in the reaction mass to provide a two-phase system. As the bisphenol-A is brominated, the tetrabromobisphenol-A is formed in the solvent. The co-produced HBr is present in the water. When used, the oxidant oxidizes the HBr to $Br_2$, which in turn is then available to brominate more bisphenol-A and its under-brominated species. By oxidizing the HBr to $Br_2$, only about two moles of $Br_2$ feed are needed per mole of bisphenol-A fed to the reactor. To recover the tetrabromobisphenol-A from the solvent, the solution is cooled until tetrabromobisphenol-A precipitation occurs. The cooling of the solution to recover tetrabromobisphenol-A entails additional expense and process time.

Highly effective process technology for producing tetrabromobisphenol-A is described in commonly-owned U.S. Pat. Nos. 5,527,971, 5,723,690, and 5,847,232, and in commonly-owned co-pending U.S. patent application Ser. Nos. 08/945,158, filed Apr. 18, 1996, 09/096,332, filed Jun. 11, 1998, and 09/149,225, filed Sep. 8, 1998. One of the factors involved in achieving the highly desirable results made possible by these commonly-owned processes is relatively close control of the amount of excess unreacted bromine in the liquid phase of the reaction mass during the bromination. In most cases this amount is maintained in the range of about 50 to about 10,000 ppm of unreacted bromine in the liquid phase of the reaction mass. Failure to keep the bromine level in the liquid phase of the reaction mass below this level especially when using a liquid bromine feed can have adverse repercussions, especially on the color characteristics of the tetrabromobisphenol-A product. In commonly-owned copending U.S. application Ser. Nos. 08/945,158 and 09/096,332, of which the present application is a continuation-in-part, a process is described wherein from about 50 to 20,000 ppm of unreacted bromine can be maintained in the liquid phase of the reaction mass by employing, inter alia, a feed stream of gaseous bromine to the reaction mass, if the feed stream has a Reynold's Number $\geq 50,000$. In this way a product having improved color, e.g., an APHA color of less than about 50, and lower ionic content can be produced.

Since the commonly-owned processes referred to above involve formation of tetrabromobisphenol-A precipitate as the bromination is proceeding, such precipitate formation can render colorimetric methods for closely assessing bromine concentration in the liquid phase of the reaction mass somewhat problematical. And while feed of vaporous bromine in the manner described in application Ser. Nos. 08/945,158 and 09/096,332, referred to hereinabove, permits greater latitude in the amount of excess bromine that can be tolerated in liquid phase of the reaction mass, it remains necessary to observe and maintain careful control over the character (e.g., Reynold's number) and quantities of the vaporous bromine being fed to the reaction mass in order to ensure production of product of acceptable color characteristics.

It would thus be of considerable advantage if a way could be found of producing tetrabromobisphenol-A of desirable minimal color with process technology that is even more tolerant of the amount of unreacted bromine in the liquid phase of the reaction mixture. And it would be particularly desirable if this objective could be achieved without sacrifice of other advantageous features of the commonly-owned technology, such as forming during the bromination precipitated tetrabromobisphenol-A that is highly pure, readily recoverable, and formed in high yield based on the bisphenol-A fed to the reaction. This invention is deemed to make possible the achievement of each of the foregoing objectives.

THE INVENTION

The processes of this invention feature the efficient production of high-quality, low-color tetrabromobisphenol-A in high yields under operating conditions that do not require such close control of the ratio between bromine and bisphenol-A fed into and maintained in the reaction mass. Indeed, it has been found possible to produce low-color tetrabromobisphenol-A pursuant to this invention with as much as about 80,000 ppm of unreacted bromine in the liquid phase of the reaction mass. Moreover, the processes of this invention can be run in the batch mode or in the continuous mode. When run in the batch mode, process efficiency is enhanced due to relatively short reactor times as there is no need for a time consuming one hour plus post-reaction cook period or a post-reaction tetrabromobisphenol-A precipitation step. The use of a continuous process for the production of tetrabromobisphenol-A is a rarity in itself and is made possible by the short reaction and tetrabromobisphenol-A precipitation times which are features of processes of this invention. In the continuous mode, reactor size can be substantially reduced without a loss in product output.

In addition to the above reaction efficiencies, the processes of this invention are capable of producing high yields of tetrabromobisphenol-A in a methanol- or ethanol-based solvent without the substantial concomitant production of methyl bromide or ethyl bromide, e.g., as little as 0.2 to 1.0 lbs (ca. 0.09 to ca. 0.45 kg) of methyl bromide or ethyl bromide per 100 lbs (ca. 45.4 kg) of tetrabromobisphenol-A product. Even further, it is possible to obtain high yields of almost pure white tetrabromobisphenol-A even though a substantial excess of unreacted bromine is present in the reaction mass.

Pursuant to this invention there is provided in one of its embodiments a process of producing tetrabromobisphenol-A which comprises:

a) contacting, during a period of time, bromine and a continuous or substantially continuous feed of bisphenol-A and/or underbrominated bisphenol-A in a reaction mass having a temperature within the range of from about 30° C. to about 100° C. and having a liquid phase comprised of a water-miscible organic solvent, e.g., methanol or ethanol, and water, in which liquid phase, tetrabromobisphenol-A is relatively insoluble;

b) during all or substantially all of the foregoing period of time, maintaining in the liquid phase of the reaction mass, an amount of HBr which will protect the color of the tetrabromobisphenol-A precipitate in d) from being adversely affected by the intentional or unintentional variance of the unreacted bromine concentration described in c) to above about 20,000 ppm and up to about 80,000 ppm;

c) during all or substantially all of the foregoing period of time, having in the liquid phase of the reaction mass, a presence of from about 50 ppm to about 80,000 ppm unreacted bromine; and d) during all or substantially all of the foregoing period of time, having tetrabromobisphenol-A precipitate from the reaction mass, normally in a yield of at least about 90% based on the amount of bisphenol-A and/or underbrominated bisphenol-A fed to the reaction mass up to that point in time.

Typically, the amount of HBr in the liquid phase of the reaction mass is, on a weight basis, from about 6 to about 50 times, and preferably from about 10 to about 20 times, as much as the maximum amount of unreacted bromine that is expected to be in the liquid phase of the reaction mass during a). In the specification and claims hereof the weights of HBr and of $Br_2$ are determined or verified by analysis using samples of the liquid phase from which precipitate has been removed. Also, reference to bromine in the liquid phase of the reaction mass should be understood to mean unreacted bromine, as distinguished from total bromine which would include both unreacted and reacted bromine.

The length of the period of time in the process of the above embodiment will usually depend upon the manner in which the process is being conducted. For example, if the process is being conducted as a batch process without removal of reaction mass or product from the reactor during the reaction, the period of time will be the relatively short time during which the reactants are being brought into contact with each other in conducting a batch process, e.g., (A) during the time bisphenol-A and/or underbrominated bisphenol-A and excess bromine are being charged to and are present in the liquid phase of the reaction mass being formed, and the reactor contents are under and comply with the conditions specified in a) through d) above so that tetrabromobisphenol-A is being produced and is precipitating, or (B) during the time bisphenol-A and/or underbrominated bisphenol-A is/are being charged to the liquid phase of the reaction mass being formed and excess bromine is present in the liquid phase of the reaction mass being formed, and the reactor contents are under and comply with the conditions specified in a) through d) above. Situation (B) can arise, for example, when:

1) during the charging of the bisphenol-A and/or underbrominated bisphenol-A, all of the excess bromine present in the liquid phase of the reaction mass being formed is being produced in situ by oxidation of HBr as described hereinafter, and the reactor contents are under and comply with the conditions specified in a) through d) above so that tetrabromobisphenol-A is being produced and is precipitating, or 2) during the charging of the bisphenol-A and/or underbrominated bisphenol-A, part of the excess bromine present in the liquid phase of the reaction mass being formed is being produced in situ by oxidation of HBr and the remainder of the excess amount of bromine is being fed to the liquid phase of the reaction mass, and the reactor contents are under and comply with the conditions specified in a) through d) above so that tetrabromobisphenol-A is being produced and is precipitating, or 3) bromine is present in a heel that is present in the reactor before the charging of bisphenol-A and/or underbrominated bisphenol-A is initiated, and during the time the feed of bisphenol-A and/or underbrominated bisphenol-A is occurring, the reactor contents are under and comply with the conditions specified in a) through d) above so that tetrabromobisphenol-A is being produced and is precipitating.

On the other hand, the period of time referred to above in connection with the process of this embodiment will be much longer when the process is being conducted on a continuous or semicontinuous basis. Indeed, since the period of time is the time during which the reactants are being brought into contact with each other in conducting the process on such basis with the reactor contents under and complying with the conditions specified in a) through d) above so that tetrabromobisphenol-A is being produced and is precipitating, the duration of such period of time is largely discretionary. This is so, because with the reactor contents under and complying with the conditions specified in a) through d) above, the reactants are being brought into contact with each other during the entire time the bisphenol-A and/or underbrominated bisphenol-A is/are being fed to the liquid phase of the reaction mass while either (A) the entire excess of bromine is being fed to the liquid phase of the reaction mass, or (B) all or part of the excess of bromine in the liquid phase of the reaction mass is being produced in situ by oxidation of HBr as described hereinafter. Concurrently, a portion of the reaction mass and precipitate is being removed from the reaction mass so that the volume of the contents of the bromination reactor remains more or less constant.

In typical, properly conducted batch operations, during at least about 80% of the foregoing period of time, and preferably during at least about 90% of the foregoing period of time, precipitate is being formed that (i) typically contains at least about 90 wt %, and preferably at least about 95 wt % of tetrabromobisphenol-A, and (ii) typically is formed in a yield of at least about 90% based on the amount of bisphenol-A and/or underbrominated bisphenol-A fed to the liquid phase of the reaction mass up to that point. In typical, properly conducted continuous operations, once steady state operation has been achieved, precipitate is continuously being formed that (i) typically contains at least about 95 wt % of tetrabromobisphenol-A, and (ii) typically is formed in a substantially continuous yield of at least about 90% based on the amount of bisphenol-A and/or underbrominated bisphenol-A that has been fed to the liquid phase of the reaction mass.

If bromine is to be generated in situ, this is best accomplished by reaction between a suitable oxidant, preferably hydrogen peroxide, and HBr. Hydrogen peroxide is preferably introduced into the liquid phase of the reaction mass in the form of a water-containing solution.

Important features of this invention are that not only is the bromination reaction very rapid especially under preferred temperature conditions used (from about 50 to about 100° C.), but during all or substantially all of the time the reactants ($Br_2$ and bisphenol-A and/or underbrominated bisphenol-A) are coming in contact with each other in the liquid phase of the reaction mass under the specified conditions, a precipitate is being formed that (i) typically contains at least about 90 wt %, and preferably at least about 95 wt % of tetrabromobisphenol-A, and (ii) typically is formed in a yield of at least about 90% based on the amount of bisphenol-A and/or underbrominated bisphenol-A fed to the reaction mass. Moreover, even though the liquid phase of the reaction mass may contain as much as 80,000 ppm of unreacted bromine, the tetrabromobisphenol-A being produced typically is of low color (e.g., it has an APHA color of 100 or less, the APHA color being determinable by dissolving 80 grams of the tetrabromobisphenol-A product in 100 mL of acetone).

Formation of the tetrabromobisphenol-A product as a precipitate facilitates the recovery of the product, as this can be effected by any of a variety of physical separation procedures such as draining, decantation, centrifugation, and/or filtration. The fact that the precipitate enriched in tetrabromobisphenol-A can be rapidly and continuously formed is of considerable advantage in that it enables the process to be conducted as a continuous process. The precipitate enriched in the desired product can be removed from the reaction mass continuously or substantially continuously, typically along with a portion of the reaction mass, whereby the volumes of feeds to, and material removed from, the reactor can be kept constant or substantially constant at all times. The presence in the liquid phase of the reaction mass of excess unreacted bromine over and above that required to convert the bisphenol-A and/or underbrominated bisphenol-A to tetrabromobisphenol-A ensures that this desired product is formed in high yield without significant contamination by under-brominated bisphenol-A such as tribromobisphenol-A. And the presence in the liquid phase of the reaction mass of the specified excess quantity of HBr relative to the unreacted bromine ensures that the tetrabromobisphenol-A product will have little, if any, undesirable color. As indicated above, the conventional wisdom in the art has been to avoid the presence of excesses of unreacted bromine above 1 wt % or at most 2 wt % in the liquid phase of the reaction mass in order to avoid color formation in the tetrabromobisphenol-A product. Yet, the practice of this invention involves deliberately keeping unreacted bromine in the liquid phase in amounts which preferably are up to about 2 wt % but which can reach as high as 8% without serious adverse consequences with respect to product color. Because of the maintenance in the liquid phase of the reaction mass of a color-protective amount of HBr relative to the targeted amount of unreacted $Br_2$ to be present in the liquid phase of the reaction mass, it is unnecessary to tightly control the amount of excess unreacted $Br_2$ in the liquid phase of the reaction mass. Thus, in conducting the processes of this invention, it is now possible to widely vary the content of bromine in the liquid phase, intentionally or unintentionally, without excessive color development in the precipitated tetrabromobisphenol-A.

Since excess bromine is to be present in the liquid phase in the reactor, the source of the bromine can consist of (i) bromine fed to the reactor in liquid and/or gaseous form or (ii) a combination of bromine fed to the reactor in liquid and/or gaseous form plus bromine generated in situ by oxidation of HBr or (iii) bromine generated in situ by oxidation of HBr. If the source of the bromine is the combination of feed bromine and in situ generated bromine, the source of the HBr subjected to the in situ oxidation can consist of (a) HBr coproduct from the bromination or (b) a combination of HBr coproduct from the bromination plus HBr fed to the reactor. While in theory it may be possible to use only HBr fed to the reactor as the source of HBr subjected to the in situ oxidation, this would require segregating the coproduct HBr from the HBr fed to the reactor. If the source of the bromine is solely in situ generated bromine, HBr is fed into the reaction mass along with a separate feed of oxidant, these feeds being proportioned to produce and maintain the excess of bromine in the liquid phase of the reaction mass, as well as to maintain an amount of HBr which will protect the color of the tetrabromobisphenol-A being precipitated from being adversely affected by the intentional or unintentional variance of the unreacted bromine concentration in the liquid phase of the reaction mass to above about 20,000 ppm and up to about 80,000 ppm.

In the practice of this invention the amount of unreacted bromine maintained in the liquid phase of the reaction mass can be as high as about 8 wt % (ca. 80,000 ppm), although typically the amount of unreacted bromine maintained in the liquid phase of the reaction mass will not exceed about 3.5 wt % (ca. 35,000 ppm). Preferably the amount of bromine in the liquid phase of the reaction mass is kept in the range of about 50 to about 20,000 parts per million (ppm) during substantially the entire bromination period. As can be seen from the foregoing, and as is conventional, all parts referred to in any portion of this document are by weight unless otherwise expressly indicated. And it will be understood that the amount of unreacted bromine in the liquid phase of the reaction mass is the total of unreacted (free) bromine in such liquid phase that originated directly from the bromine fed to the reactor, and any unreacted (free) bromine that may be generated in situ in such liquid phase by oxidation of coproduct HBr formed in the bromination, if such oxidation is employed in the process.

In accordance with another embodiment of this invention, tetrabromobisphenol-A can be produced by a process which comprises:
  a) feeding to a reactor, at least bisphenol-A and/or underbrominated bisphenol-A, bromine, water, and a water-miscible organic solvent, to at least partially form a reaction mass having a liquid phase containing from above about 15 to about 85 wt % water, the wt % being based upon the amount of water and water-miscible organic solvent in the liquid phase; and
  b) during at least a substantial portion of a), (i) providing for the presence in the liquid phase of the reaction mass of an amount of unreacted bromine that is in excess over the stoichiometric amount theoretically required to convert the bisphenol-A and/or underbrominated bisphenol-A to tetrabromobisphenol-A, and to continuously form during substantially all of the time the feeding in a) is occurring, a precipitate comprised mainly of tetrabromobisphenol-A, the yield of precipitated tetrabromobisphenol-A during substantially all of the time the feeding in a) is occurring being at least about 90% based on the amount of the bisphenol-A or underbrominated bisphenol-A or combination thereof fed up to that point in time, and (ii) providing for an amount of HBr in the liquid phase of the reaction mass which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm.

In conducting this embodiment of the invention the temperature of the liquid phase of the reaction mass is typically in the range of about 30 to about 100° C. and preferably is a temperature which is within the range of from about 50 to about 100° C. If an oxidant is included in the feed to the reactor, a portion of the HBr coproduct is oxidized in situ to produce additional bromine in the liquid phase of the reaction mass. Thus the amount of oxidant, if used, should be controlled so that the amount of HBr present in the liquid phase of the reaction mass is sufficient to protect the tetrabromobisphenol-A against excessive color formation taking into consideration the maximum amount of unreacted bromine that may be expected to be in the liquid phase during the feeding of the reactants. If desired, HBr with or without oxidant can be included in the feed to the reactor, again provided that the amount of HBr is sufficient to protect the tetrabromobisphenol-A against excessive color development therein.

Also in accordance with this invention, tetrabromobisphenol-A can be produced by a co-feed process which comprises:
  a) co-feeding $Br_2$ and a solution comprised of bisphenol-A and/or underbrominated bisphenol-A, water and a water-miscible organic solvent to a reactor to at least partially form a reaction mass having a liquid phase and a solids phase, the liquid phase containing water in an amount of from above about 15 to about 85 wt % water, the wt % being based upon the amount of water and water-miscible organic solvent in the liquid phase, the solids phase comprising predominately a precipitate of tetrabromobisphenol-A;
  b) the reaction mass liquid phase containing during all or substantially all of the time the co-feeding in a) is taking place, an amount of unreacted bromine that is in excess over the stoichiometric amount theoretically required to convert the bisphenol-A and/or underbrominated bisphenol-A to tetrabromobisphenol-A, such that during substantially all of the time of the co-feeding in a), the tetrabromobisphenol-A is being produced in a yield of at least about 90% based on the amount of the bisphenol-A and/or underbrominated bisphenol-A already fed;
  c) the reaction mass liquid phase also containing during all or substantially all of the time the co-feeding in a) is taking place, an amount of HBr which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm; and
  d) periodically or continuously removing tetrabromobisphenol-A precipitate from the reactor along with a portion of the reaction mass so that the volume of the reaction mass in the reactor remains substantially constant.

In this embodiment of the invention it is again preferable to have a reaction mass temperature which is within the range of from about 50 to about 100° C.

In this co-feed process the formation of the reaction mass can best be accomplished by co-feeding (1) the $Br_2$ and (2) a bisphenol-A/water/solvent solution, or a bisphenol-A and underbrominated bisphenol-A/water/solvent solution or slurry, or an underbrominated bisphenol-A/water/solvent solution or slurry. By co-feeding, is meant that the $Br_2$ and the solution or slurry feed periods overlap one another to at least some extent. (A feed period is that period of time over which all of a subject feed is fed to the reactor.) For example, the $Br_2$ feed can be initiated and then followed by the solution or slurry feed, with both feeds thereafter occurring simultaneously until finished. Another example would be that of an initial $Br_2$ feed followed by a continuous solution or slurry feed which is accompanied by a continued, but intermittently interrupted or staged, $Br_2$ feed. Yet another example is that of initiating the $Br_2$ feed followed by the solution or slurry feed so that the two feeds occur simultaneously until the specified amount of $Br_2$ has been fed. At that point, the solution or slurry feed continues alone until it is finished. Other co-feed schemes could feature an intermittently interrupted solution or slurry feed, or initially feeding the solution or slurry into a $Br_2$ containing reactor followed by a combined $Br_2$ and solution or slurry feed. It is also possible to conduct this embodiment such that the $Br_2$ and the solution or slurry feeds are, timewise, completely concurrent one with the other. Still other variants include substantially concurrent or completely concurrent but separate feeds of (a) $Br_2$, (b) a bisphenol-A/water/solvent solution, and (c) a bisphenol-A and underbrominated bisphenol-A solution or slurry, or a slurry of underbrominated bisphenol-A. Similarly, it is possible, especially in a continuous mode of operation, to use alternating feeds such as by concurrently but separately feeding (a) $Br_2$, and (b) a bisphenol-A/water/solvent solution for a certain period of time, and then switch for a certain period of time to concurrent but separate feeding of (a) $Br_2$ and (b) a bisphenol-A and underbrominated bisphenol-A/water/ solvent solution or slurry, or an underbrominated bisphenol-A/water/solvent slurry. These and still other co-feeding variants will now be readily apparent to those skilled in the art.

Feeds that do not have some overlap of the $Br_2$ and solution feed periods are possible, but will not be generally preferred. For example, all of the $Br_2$ can be fed followed by the solution or slurry feed. However, depending on reaction conditions, such a feed scheme could lead to the formation of undesirable by-products due to the high concentration of $Br_2$ which is seen by the initial bisphenol-A and/or underbrominated bisphenol-A feed. Another scheme, i.e., feeding large amounts of bisphenol-A and or underbrominated bisphenol-A before feeding $Br_2$, would not be preferred as it could lead to precipitation of substantial amounts of tribromobisphenol-A.

When carrying out the above co-feed process, whatever the manner of conducting the feeding, it must be in harmony with the requirements of steps b), c) and d) of the co-feed process.

Another embodiment is a process for the production of tetrabromobisphenol-A, which process comprises:
  a) feeding to a reactor, bisphenol-A and/or underbrominated bisphenol-A, hydrogen bromide, an HBr oxidant, water, and a water-miscible organic solvent, to partially form a reaction mass having a liquid phase containing in the range of from above about 15 to about 85 wt % water, and typically in the range of about 30 to about 85 wt % water, the wt % being based upon the amount of water and water-miscible organic solvent in the liquid phase; and
  b) proportioning the feeds in a) such that during at least a substantial portion of the time when both the feeding and the bromination of bisphenol-A and/or underbrominated bisphenol-A are taking place, there is present in the liquid phase of the reaction mass (i) an amount of unreacted bromine that is in excess over the stoichiometric amount theoretically required to convert the bisphenol-A to tetrabromobisphenol-A, and (ii) an amount of HBr which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm, to continuously form during substantially all of the time when both the feeding and the bromination are taking place, a precipitate comprised mainly of tetrabromobisphenol-A, the yield of precipitated tetrabromobisphenol-A during substantially all of the time when both the feeding and the bromination are taking place being at least about 90% based on the amount of the bisphenol-A and/or underbrominated bisphenol-A fed up to that point in time.

Still another embodiment of this invention is a process for the production of tetrabromobisphenol-A, which process comprises:
  a) brominating bisphenol-A and/or underbrominated bisphenol-A by feeding bisphenol-A and/or underbrominated bisphenol-A to a reaction mass having a reaction mass temperature which is in the range of from about 30 to about 100° C., and having a liquid phase, which liquid phase contains (i) water and a solvent quantity of a water-miscible organic solvent, the water being present in an amount of from about 30 to about 85 wt %, and preferably within the range of about 30 to about 75 wt %, based on the weight of the water and water-miscible organic solvent in the reaction mass, and (ii) 50 to 80,000 ppm of unreacted $Br_2$ so that a precipitate containing at least about 95 wt % of tetrabromobisphenol-A is being formed substantially continuously during the time such feeding is taking place; and
  b) during substantially all of the time the feeding in a) is taking place, having in the liquid phase of the reaction mass an amount of HBr sufficient to protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm.

Another embodiment of this invention is a process for the production of tetrabromobisphenol-A, which process comprises:
  a) brominating bisphenol-A and/or underbrominated bisphenol-A by feeding bisphenol-A and/or underbrominated bisphenol-A to a reaction mass having a reaction mass temperature which is in the range of from about 30 to about 100° C. (preferably in the range of from about 50 to about 100° C., and most preferably in the range of from about 50 to about 80° C.), and having a liquid phase, which liquid phase contains (i) water and a solvent quantity of a water-miscible organic solvent (preferably an alcohol having up to 4 carbon atoms, and most preferably methanol, ethanol or a mixture thereof), the water being present in an amount of from about 30 to about 85 wt %, and preferably in the range of about 30 to about 75 wt %, based on the weight of the water and water-miscible organic solvent in the reaction mass, and (ii) at least about 50 ppm but no more than about 80,000 ppm (preferably no more than about 35,000 ppm, and most preferably up to about 20,000 ppm), of unreacted $Br_2$ to continuously produce during at least a substantial portion of the feeding in a), a precipitate enriched in tetrabromobisphenol-A, such tetrabromobisphenol-A being produced in a yield of at least about 90% based on the amount of bisphenol-A and/or underbrominated bisphenol-A already fed to the reaction mass;
  b) during at least a substantial portion of the feeding in a), having in the liquid phase of the reaction mass an amount of HBr sufficient to protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm; and c) during at least a substantial portion of the feeding in a), continuously removing at least a portion of the precipitate from the reaction mass.

Typically, the process is conducted such that a precipitate is produced which is at least 95 wt % tetrabromobisphenol-A and in a yield which is at least about 90%, based on the amount of bisphenol-A and/or underbrominated bisphenol-A fed. Also, the tetrabromobisphenol-A produced typically has an APHA color of less than about 100, preferably 50 or less, the APHA color being determinable by dissolving 80 grams of the tetrabromobisphenol-A product in 100 mL of acetone. It is to be noted that if the specified excess of HBr relative to $Br_2$ in the liquid phase of the reaction mass pursuant to this invention is not utilized, it is desirable to control the amount of unreacted bromine in such liquid phase to from about 2000 to about 6000 ppm.

In conducting the process of this embodiment it is often desirable to provide at least a portion of the unreacted $Br_2$ by the oxidation of HBr to $Br_2$. This oxidation is preferably conducted by introducing an oxidant, preferably aqueous hydrogen peroxide, into the reaction mass, preferably continuously. However, it is possible, though not preferred, to withdraw, periodically or continuously, a portion of the reaction mass from the bromination reactor, treat the withdrawn portion with the oxidant externally of the bromination reactor in a closed system, and then return the treated portion of the reaction mass to the bromination reactor. Also, when conducting a process pursuant to this embodiment it is preferred to continuously remove at least a portion of the precipitate from the reaction mass.

This invention in its various forms referred to above thus provides in essence a process wherein tetrabromobisphenol-A product is produced by providing a liquid phase reaction system in which there is directly formed a tetrabromobisphenol-A precipitate by the bromination of bisphenol-A and/or underbrominated bisphenol-A. The bromination involves use of an excess of bromine over the stoichiometric amount theoretically required to produce tetrabromobisphenol-A. Also, the bromination is conducted in the presence of an amount of HBr that is high enough to protect the tetrabromobisphenol-A being produced from excessive color development taking into consideration the maximum amount of unreacted bromine that is targeted or expected to be present in liquid phase of the reaction mass during the time the bromine and bisphenol-A and/or underbrominated bisphenol-A are being brought together in the liquid phase of the reaction mass. Moreover, the bromination is conducted at such rate that (i) there is insufficient opportunity for significant precipitation of the intermediate, tribromobisphenol-A, to occur, and (ii) while the bisphenol-A and/or underbrominated bisphenol-A is/are being brought into contact with unreacted bromine in the liquid phase of the reaction mass, tetrabromobisphenol-A is being produced substantially continuously. Typically the yield of the tetrabromobisphenol-A as it is being produced substantially continuously is at least about 90% based on the amount of the bisphenol-A and/or underbrominated bisphenol-A already fed. In addition the tetrabromobisphenol-A produced typically has an APHA color of less than about 100, preferably 50 or less, the APHA color being determinable by dissolving 80 grams of the tetrabromobisphenol-A product in 100 mL of acetone. And when the process is conducted as a continuous process under preferred constant steady state conditions, where, inter alia, the total volume of uniform feeds to the bromination reactor and the total volume of some reaction mass plus continuously-forming precipitate being withdrawn from the reactor are kept substantially constant and substantially equal at all times, (i) the precipitate is continuously produced in a yield of at least about 90% based on the amount of bisphenol-A and/or underbrominated bisphenol-A being fed up to that point in time, (ii) the tetrabromobisphenol-A being continuously produced has an APHA color of less than about 100, preferably 50 or less, and (iii) the precipitate as it is continuously being formed and withdrawn from the reactor contains at least about 95 wt % tetrabromobisphenol-A.

A further embodiment to this invention is a process for protecting tetrabromobisphenol-A against excessive color development during its production by bromination of bisphenol-A and/or underbrominated bisphenol-A by bromine, which process comprises:

a) feeding bisphenol-A and/or underbrominated bisphenol-A to a reaction mass having during all or substantially all of the time such feeding is taking place, a liquid phase in which tetrabromobisphenol-A is relatively insoluble comprising water and a water-miscible organic solvent;

b) during all or substantially all of the time the feeding in a) is taking place, having in the liquid phase at least about 50 ppm but not more than about 80,000 ppm of unreacted bromine and having the temperature in the liquid phase in the range of from about 30 to about 100° C.;

c) during all or substantially all of the time the feeding in a) is taking place, having the water and the organic solvent proportioned in the liquid phase at a weight ratio within the range of from about 30:70 to about 85:15 that enables a precipitate containing tetrabromobisphenol-A to be formed substantially continuously during substantially the entire time the feeding in a) is taking place, and in a substantially continuous yield of at least 90% based on the amount of bisphenol-A and/or underbrominated bisphenol-A already fed in accordance with a) up to that time; and d) during all or substantially all of the time the feeding in a) is taking place, maintaining the relative proportions of HBr and $Br_2$ in the liquid phase of the reaction mass such that there is present therein an amount of HBr relative to the amount of bromine that will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm.

Other embodiments and features of the invention will become still further apparent from the ensuing description and appended claims.

Commercially available $Br_2$ is suitable for use as the $Br_2$ feed. Should the $Br_2$ contain undesirable impurities, it can be treated by conventional purification techniques, e.g., distillation, $H_2SO_4$ treatment, etc., which are well known to those skilled in the art.

The $Br_2$ can be fed as a liquid or as a gas to the reactor. It is preferred that the feed be gaseous. Whether the $Br_2$ is liquid or gaseous, it is preferred that the feed entry point be sub-surface of the reaction mass. This is conveniently accomplished by use of a dip tube. If the feed is liquid, above-surface feed must contend with possible splattering, bromine loss due to evaporation, and inefficient mixing.

The amount of water in the reaction mass should be within the range of from above about 15 to about 85 wt %, and typically is in the range of about 30 to about 85 wt % of water, based upon the total amount of water and water-miscible organic solvent in the liquid phase of the reaction mass. Preferably, the amount of water fed is that amount which is within the range of from about 30 to about 75 wt % water. Most highly preferred is the range of from about 30 to about 70 wt %. When the water-miscible organic solvent is methanol the preferred amount is from about 30 to about 55 wt %. With ethanol, the preferred amount of water is from about 40 wt % to about 65 wt %.

The water content of the reaction mass is an important aspect of this invention. It is believed, though the processes of this invention are not to be limited by any particular theory, that the water content suppresses formation of methyl bromide or ethyl bromide and, at the same time, allows for production of high purity tetrabromobisphenol-A product. Normally, it might be expected that the water content would cause under-brominated species, e.g., tribromobisphenol-A, to precipitate along with the tetrabromobisphenol-A species, thereby yielding an impure product. However, the processes of this invention are in fact capable of producing product of desirable purity as well as product with little, if any, color.

In the co-feed process it is convenient and preferred to feed the water to the reactor as part of a solution or slurry which also contains bisphenol-A and/or underbrominated bisphenol-A and a water-miscible solvent. However, the water may be introduced into the reaction mass in other equivalent ways. For example, the water can be fed as a separate feed stream. Such a feed could be essentially contemporaneous with the feed of a solution or slurry of bisphenol-A and/or underbrominated bisphenol-A and water-miscible solvent. Even further, a portion, if not all, of the water can be fed as steam or steam condensate along with a gaseous $Br_2$ feed. The steam could have been used to vaporize the $Br_2$ to form the gaseous feed. Another example features providing water as a charge or as part of a charge to the reactor prior to initiating the feeds and adjusting the amount of water later fed to obtain the desired water content in the reaction mass. No matter how the water is provided to the reaction mass, the only requirement for the water feed is that the proper amount of water be present in the reaction mass during substantially all of the reaction period so that precipitation of tetrabromobisphenol-A occurs as the bromination is proceeding.

In those cases where the amount of water used is in the lower end of the range of about 15 to about 85 wt %, say 15 to 25 or 30 wt %, it may be desirable in batch operations to add some additional water at the end of the bromination of the bisphenol-A and/or underbrominated bisphenol-A to cause additional precipitation of tetrabromobisphenol-A from the reaction mass. In such cases, the added water is counted in the total solution water.

The water-miscible organic solvent is preferably fed to the reactor as a constituent of a solution or slurry of bisphenol-A and/or underbrominated bisphenol-A. However, if desired, a portion of the organic solvent can be fed as part of the bisphenol-A and/or underbrominated bisphenol-A solution or slurry, with the remaining portion, generally a smaller portion, being fed as a separate stream. Also, in the event HBr and/or an oxidant such as hydrogen peroxide is/are to be fed to the reactor, a portion of the water can be introduced into the reaction mass in the form of aqueous HBr and/or aqueous hydrogen peroxide.

From the above it can be seen that the organic reactant used in the practice of this invention is bisphenol-A and/or underbrominated bisphenol-A. The term "underbrominated bisphenol-A" refers to one or more brominated bisphenol-A compounds in which less than the four ortho-positions relative to the hydroxyl groups are substituted by a bromine atom. Typically, the major underbrominated bisphenol-A species is the tribrominated species (3,5-dibromo-4-hydroxyphenyl)(3-bromo-4-hydroxyphenyl) dimethylmethane), but one or more other underbrominated species may be present such as either or both of the dibromo species, 3,5-dibromo-4-hydroxyphenyl)(4-hydroxyphenyl) dimethylmethane and bis(3-bromo-4-hydroxyphenyl) dimethylmethane, and/or the monobromo species (3-bromo-4-hydroxyphenyl)(4-hydroxyphenyl)dimethylmethane. Therefore, the organic reactant fed to the reactor can be bisphenol-A only, any one of these underbrominated bisphenols only, any combination of any two or more of these underbrominated bisphenol-A species only, or any combination of bisphenol-A and any one or more of these underbrominated bisphenol-A species. The preferred organic reactant fed to the reactor is bisphenol-A itself. Of course, during the bromination, the bisphenol-A is transformed into various underbrominated bisphenol-A species until it becomes tetrabromobisphenol-A. The same holds true for the various underbrominated bisphenol-A species which during bromination finally become tetrabromobisphenol-A. Therefore, the term "bisphenol-A and/or underbrominated bisphenol-A" in this document refers to the identity of the compound as it exists prior to being fed into the bromination reaction mass.

As can be appreciated from the foregoing, the manner in which the water, solvent, solution and/or slurry can be fed is not critical to the processes of this invention provided that the reaction mass is properly constituted. Thus, to simplify matters for discussion, reference is made to the feed of a solution which comprises bisphenol-A, water and water-miscible solvent. Such reference is to be understood to mean that the water can be fed as a constituent of the solution, as a separate stream or as a combination of both, and that the organic solvent can all be fed as a constituent of the solution or as a portion in the solution and as a portion in a separate stream. Also to be considered as part of the solution feed is any water or organic solvent which is provided to the reaction mass as a pre-feed charge or as a part of such a charge to the reactor. Such reference to the feed of such solution is also to be understood to serve in the same way as an illustration by analogy of the feed of a solution or slurry of one or more underbrominated bisphenol-A species with or without bisphenol-A, water and water-miscible solvent. In short, whatever is illustrated with reference to this particular solution is intended to apply to the extent possible to analogous feed solutions or slurries referred to elsewhere in this document.

The water-miscible organic solvent can be defined functionally as a material which is capable of solvating $Br_2$ bisphenol-A, monobromobisphenol-A, dibromobisphenol-A and tribromobisphenol-A under reaction conditions. Further, the organic solvent should be substantially inert with regard to $Br_2$, $H_3OBr$ and the ring-bromination of the bisphenol-A to tetrabromobisphenol-A and not contribute to the production of troublesome amounts of color bodies, ionic bromides and/or hydrolyzable bromides. Hydrolyzable bromides can include 1-bromo-2-alkoxy-2-(3',5'-dibromo-4'-hydroxyphenyl)propane, 1,1-dibromo-2-alkoxy-2-(3',5'-dibromo-4'-hydroxyphenyl)propane, 1,3-dibromo-2-alkoxy-2-(3',5'-dibromo-4'-hydroxyphenyl)propane, and 1,1,3-tribromo-2-alkoxy-2-(3',5'-dibromo-4'-hydroxyphenyl) propane. The solvent, when taken in combination with the water and reaction conditions of the processes of this invention, can have some small ability to solvate tetrabromobisphenol-A, but for the sake of reaction yield, the solvating power should be low, say no more than about 20 wt % and preferably no more than about 5 wt % solvated tetrabromobisphenol-A in the liquid phase of the reaction mass.

Exemplary of the preferred water-miscible organic solvents are water-miscible alcohols (e.g., methyl alcohol, ethyl alcohol, n-propyl alcohol, isopropyl alcohol, tert-butyl alcohol), water-miscible carboxylic acids, (e.g., acetic acid, propionic acid), and water-miscible nitriles, (e.g., acetonitrile). Some water-miscible ethers may also be suitable provided they are not cleaved by the acidic nature of the reaction mass. The more preferred solvents are the alcohols having up to 4 carbon atoms. Most preferred are ethanol and methanol as they are relatively inexpensive and are easily recovered by simple distillation techniques for recycle. It is to be understood and appreciated that the organic solvent need not be soluble in water in all proportions at, say, 20° C. Although such total miscibility is preferable, the organic solvent should at least have sufficient solubility in water in the proportions and at the bromination temperature(s) being employed to form a clear one-phase homogeneous liquid reaction medium from which tetrabromobisphenol-A product will precipitate during the bromination.

The amount of water-miscible organic solvent used is best related to the amount of bisphenol-A fed and can be conveniently expressed as the weight ratio of the organic solvent to bisphenol-A. Typically, the ratio is within the range of from about 1:1 to about 10:1, preferably within the range of from about 2:1 to about 10:1, and most preferably the ratio is within the range of from about 3:1 to about 5:1. More or less organic solvent can be used, provided that the solvent function mentioned above is accomplished.

When the water-miscible organic solvent used is ethanol, it is preferred to produce no more than about 4.54 kg (10 lbs) of ethyl bromide per 45.4 kg (100 lbs) of tetrabromobisphenol-A precipitate produced.

The $Br_2$ and solution feed streams are preferably at a temperature which promotes process efficiency in view of the desired reaction mass temperature. A suitable liquid $Br_2$ feed temperature is from about 1° C. to just below the boiling point of $Br_2$. If the $Br_2$ is to be fed as a gas, then the $Br_2$ stream temperature should be that which is conducive to such a feed. For example, such a feed temperature may be within the range of from about 60 to about 100° C. The solution feed temperature should be that which does not detrimentally cool or heat the reaction mass or which requires pressure operation so that the feed can be made in the liquid state. If the solution feed is to be made with separate water and/or organic solvent feeds, then the same comments made above with regard to temperature apply to the separate feeds.

The $Br_2$ and solution and/or separate water, etc., feeds all contribute to the formation of the reaction mass in the reactor. These feeds will produce a reaction mass liquid phase (liquid portion) and, because of the formation of tetrabromobisphenol-A precipitate, ultimately a reaction mass solid phase (solid portion). At least a portion of the $Br_2$ feed, be it fed as a gas or as a liquid, will be consumed in the bromination reaction. Any non-consumed $Br_2$ feed will be found in the liquid phase and, if an oxidant is used, will be joined there by any non-consumed $Br_2$ produced by the oxidation of HBr present in the reaction mass.

Preferably, unreacted bromine in the liquid phase of the reaction mass is present as the solution is being fed. It is permissible for the unreacted $Br_2$ content in the reaction mass to disappear for brief periods of time depending on the level of under-brominated species that can be tolerated in the tetrabromobisphenol-A reaction product and/or upon the extent of precipitation of the underbrominated species which is experienced. In fact, if the period of time is very brief and favorable reaction parameters are chosen, the formation of these underbrominated precipitates may not occur to any appreciable extent. It is thus desirable when establishing the process parameters to be used in a given situation to observe the process and determine by empirical methods the sensitivity of the chosen reaction conditions to the brief absence of unreacted $Br_2$ in the reaction mass. Thus, for the purposes of this invention the feature of maintaining in the liquid phase of the reaction mass an amount of unreacted bromine that is in excess over the stoichiometric amount theoretically required to convert the bisphenol-A to tetrabromobisphenol-A encompasses brief periods of time in which the unreacted bromine content can be nil, but which does not result in the formation of underbrominated species to an extent that results in an unacceptable tetrabromobisphenol-A product, say, one containing less that about 96 wt % tetrabromobisphenol-A.

Quantifying for a selected set of operating conditions the preferred target amount of unreacted $Br_2$ to be present in the reaction mass liquid phase is best handled by a trial and error technique. A trial process is first defined by choosing an unreacted $Br_2$ target level and the other process parameters. The produced tetrabromobisphenol-A product from the process is analyzed for its tri- and tetrabromobisphenol-A content. If the tribromobisphenol-A level is too high, another trial process is constructed with a higher target unreacted $Br_2$ level. The procedure is repeated until the desired product is obtained. (Note that some benefit towards reducing the tribromobisphenol-A content can also be obtained by using a higher reaction temperature.) As the chosen unreacted $Br_2$ content gets higher, care should be taken that the unreacted $Br_2$ content will not be so high that it results in the production of tribromophenol and other by-products which are not desirable from a commercial standpoint. As indicated above, as long as the proposed operation is designed so that ample HBr is being maintained in the liquid phase to protect the tetrabromobisphenol-A against excessive color formation, relatively wide fluctuations in bromine content in the liquid phase to above about 20,000 ppm and up to about 80,000 ppm, whether intentional or unintentional, during bromination can readily be tolerated without adverse color formation in the tetrabromobisphenol-A product being produced.

Quantitative determination of the amounts of unreacted bromine and HBr in the liquid phase of the reaction mass is best conducted by sampling the reaction mass at intervals during the bromination, removing solids from the samples and analyzing the samples for their contents of bromine and HBr. While the particular methods of analysis used are not critical as long as they are of suitable accuracy and precision, the following overall analytical procedures are recommended:

Determination of Unreacted Bromine:

A weighed aliquot of the clear reaction mass mother liquor (about 1 mL sample) is dispersed into 100 ml of 2% potassium iodide solution. Starch is added as an indictor. Blue color indicates the presence of bromine. The stirred mixture is titrated against 0.01 N sodium thiosulfate solution to a clear end point. Unreacted bromine is calculated as follows:

$$\text{Wt \% Bromine} = \frac{\text{mL of sodium thiosulfate} \times \text{Normality of sodium thiosulfate} \times 8}{\text{Sample weight in grams}}$$

Determination of Hydrogen Bromide:

A weighed aliquot (about 1 mL sample) of the clear reaction mass mother liquor is mixed with 50 mL of deionized water. About 10 drops of 0.1% aqueous bromocresol green indicator solution is added and titrated with 0.5N NaOH solution to a blue end point. Amount of hydrogen bromide is calculated as follows:

$$\text{Wt \% HBr} = \frac{\text{mL of NaOH} \times \text{Normality of NaOH} \times 8.091}{\text{Sample weight in grams}}$$

As noted above, an important feature of this invention is maintaining in the liquid phase of the reaction mass, an amount of HBr which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm. By virtue of this feature, close control of the unreacted bromine content in the liquid phase is unnecessary—wide fluctuations can be tolerated without material adverse consequences such as excessive color development in the product. Thus continual monitoring of unreacted bromine content in the liquid phase is unnecessary, especially once steady state reaction conditions are in place. From then on only periodical monitoring is necessary to ensure that the process is functioning pursuant to this invention. Moreover, once the steady state conditions are in place, the frequency of HBr analyses can be reduced to periodical checking to be sure that some upset such as line pluggage or etc. has not occurred.

It is possible to estimate the unreacted $Br_2$ content of the liquid phase of the reaction mass by the use of colorimetric techniques. A technique which can be used comprises the formation of an acidic (HBr) water and methanol or ethanol solution. From this solution, several standard samples are prepared, to each of which is added a different and measured amount of $Br_2$. The colors of these sample solutions are then compared colorimetrically with the color of the liquid of phase of the reaction mass. A color match is indicative of the amount of $Br_2$ in the liquid phase. Colorimetric determination for unreacted $Br_2$ is quite suitable as unreacted $Br_2$ colors the sample solutions and the reaction mass in accordance with its concentration. Low concentrations give a pale yellow color; intermediate concentrations give a strong yellow color; high concentrations give an orange color; and the highest concentrations give a dark red color. Unreacted $Br_2$ concentrations in excess of about 10,000 ppm, based upon the reaction mass liquid portion, are preferred, although smaller excesses above stoichiometric can be used. As noted above, an excess of as high as about 80,000 ppm of unreacted bromine in the liquid phase can be used although typically the excess will not be above about 35,000 ppm, with the most preferred amount of unreacted bromine being within the range of from about 50 to about 20,000 ppm.

The unreacted $Br_2$ concentrations are maintained in the reaction mass so long as bisphenol-A and underbrominated species are likewise present. As can be appreciated, the unreacted $Br_2$ content diminishes as the $Br_2$ reacts, thus, the $Br_2$ feed acts to replenish the $Br_2$ in the reaction mass. Using the above-described colorimetric technique, the unreacted $Br_2$ content of the reaction mass can be monitored during the process and the unreacted $Br_2$ content within the chosen target range can be maintained by adjusting the $Br_2$ feed, the solution feed or both. Since there will be tetrabromobisphenol-A precipitate in the reaction mass, colorimetric monitoring may require that a small stream be taken from the reactor and filtered to remove the solids before being submitted to a colorimetric technique. It may also be possible to read the intensity of the reaction mass color without filtration by the use of reflectance techniques which measure the intensity of the light reflected off of the reaction mass. In all of the colorimetric cases, the color of the liquid phase of the reaction mass can be used as the determinative factor.

It is also to be understood that the method used to obtain the desired unreacted $Br_2$ level can be by a method other than the adjustment of the before-mentioned feeds. For example, when an oxidant is used to convert HBr to $Br_2$, the amount of $Br_2$ generated can be regulated by controlling the amount of oxidant fed to the reaction mass. The amount of unreacted $Br_2$ contributed to the reaction mass by oxidation of HBr can be substantial considering that four moles of HBr are generated for each mole of tetrabromobisphenol-A produced. Thus, when additional $Br_2$ is needed, oxidation of HBr can be used to generate at least a part of the $Br_2$ needed to obtain the desired unreacted $Br_2$ level.

With the use of an oxidant to oxidize the HBr to $Br_2$, the processes of this invention can obtain good results by feeding only about two moles or slightly more of $Br_2$ to the reactor for every one mole of bisphenol-A fed. The other two moles of $Br_2$ that are needed are provided by the full oxidation of the co-generated HBr. If there is less than full HBr oxidation, then the amount of $Br_2$ fed to the reactor will be that amount, in sum with the $Br_2$ formed by oxidation, which will provide quantities of $Br_2$ which are in excess of stoichiometric. Stoichiometric $Br_2$ for the ring-tetrabromination of bisphenol-A is four moles of $Br_2$ per mole of bisphenol-A. As can be appreciated, when oxidation of HBr is not part of the process, then the $Br_2$ feed will be in excess of four moles of $Br_2$ per mole of bisphenol-A fed.

In a case where both bisphenol-A and underbrominated bisphenol-A, or one or more underbrominated bisphenol-A species without bisphenol-A are fed to the bromination reactor, the stoichiometric excess of bromine is also present preferably at any given time in the liquid phase reactor. A stoichiometric amount of bromine is one molecule of diatomic bromine ($Br_2$) for each hydrogen atom present as a substituent in an ortho-position relative to the hydroxyl groups of bisphenol-A and/or underbrominated bisphenol-A fed to the reactor. For example, if the feed were 1 mole of bisphenol-A and 1 mole of tribromobisphenol-A, there would be a total of 5 moles of hydrogen atoms in the ortho positions—i.e., 4 moles in the bisphenol-A and 1 mole in the tribromobisphenol-A. A stoichiometric amount of bromine in this particular case would therefore be equivalent to 5 moles of diatomic bromine, and pursuant to this invention an amount of bromine equivalent to more than 5 moles of bromine would be fed into the liquid phase of the reaction mass, or fed into the liquid phase of the reaction mass and generated in situ, or generated in situ. Similarly, if the feed were, say, 1 mole of monobromobisphenol-A, there would be a total of 3 moles of hydrogen atoms in the ortho positions. A stoichiometric amount of bromine in this particular case would therefore be equivalent to 3 moles of diatomic bromine, and pursuant to this invention an amount of bromine equivalent to more than 3 moles of bromine would be maintained in the liquid phase of the reaction mass. Whatever the manner used in providing the excess unreacted bromine in the liquid phase of the reaction mass, the amount of unreacted bromine specified above should be maintained in the liquid phase of the reaction mass.

While on the subject of stoichiometry, it will be understood that for every atom of bromine introduced into the bisphenol-A or underbrominated bisphenol-A molecule during the bromination, one molecule of HBr is produced. In other words, for every mole of diatomic bromine ($Br_2$) that reacts with the bisphenol-A or underbrominated bisphenol-A, one mole of HBr coproduct is produced. Therefore this HBr that is automatically generated in situ should be taken into consideration in designing the feeds and feed rates to be used in the reaction in order to maintain the requisite amount of HBr in the liquid phase of the reaction mixture. Although most of such coproduct HBr will usually remain in the liquid phase, some HBr may escape into the headspace of the reactor. The amount of such vaporized HBr will depend on such factors as the rate at which the bromination reaction is proceeding, the amount of water present in the liquid phase, the rate of agitation, if any, being used, and the pressure conditions in the reactor. Therefore, in any given situation where the conditions for producing and maintaining the particular amount of HBr desired in the liquid phase of the reaction mass during the time the reactants are being brought into contact with each other so that bromination is taking place, are not already known, it is desirable to perform a few preliminary pilot experiments in which the calculated feeds are adjusted to achieve the optimal conditions for achieving the desired amount of HBr in the liquid phase of the reaction mass.

Irrespective of the $Br_2$ source, the stoichiometric excess is desirable since it is less difficult to control the process by having excess $Br_2$ present at least during most of the reaction period. For batch processes, the excess $Br_2$ present after completion of the process can be removed by treating the reaction mass with a reducing agent such as sodium sulfite or hydrazine.

It is possible to use oxidant materials to generate additional bromine in situ in any situation in which this is desirable. The oxidant must be capable of oxidizing HBr to $Br_2$ in the reaction masses and under the process conditions of this invention and without interfering with the bromination reaction. Chlorine in small proportions may be used as the oxidant, but hydrogen peroxide is the preferred oxidant. When and if using $H_2O_2$, safety considerations make it desirable to feed it to the reaction mass as an aqueous solution containing no more than about 90 wt % $H_2O_2$. Preferred are aqueous solutions containing from about 30 to about 80 wt % $H_2O_2$. A most preferred solution is one containing from about 50 to about 70 wt % $H_2O_2$.

Hydrogen peroxide can be fed to the reaction mass at any time. When resorting to its use in a batch operation, the $H_2O_2$ is preferably fed after most of the $Br_2$, e.g., above about 50%, has been fed. For continuous operation, the $H_2O_2$ feed most preferably occurs contemporaneously with at least most of the $Br_2$ feed. Most preferably, the $H_2O_2$ feed would start after initiating the $Br_2$ feed.

Unless the color of the final product is of no importance, the amount of oxidant fed must not reduce the amount of HBr present in the liquid phase to below the amount necessary for protecting the tetrabromobisphenol-A against adverse color formation in the event of intentional or unintentional variance of the unreacted bromine concentration to a concentration in the range of from above about 20,000 ppm to about 80,000 ppm. Thus if oxidant is to be fed to the reactor, it can prove useful to also feed HBr to the reactor in an amount that will ensure the presence in the liquid phase of such color-protecting amount of HBr.

Another important consideration in practicing the processes of this invention is the reaction mass temperature during the bromination period. It is desirable to use a relatively high temperature so that the bromination of the bisphenol-A to tetrabromobisphenol-A will be sufficiently fast to reduce the extent of tribromobisphenol-A precipitate formation. However, there is a practical limit as to how high the temperature can be. For example, temperatures which would cause the production of unacceptable levels of unwanted by-products or the degradation of the tetrabromobisphenol-A product should not be used.

It is unusual to operate a tetrabromobisphenol-A process at relatively high temperatures, especially when production of a co-product such as methyl bromide or ethyl bromide is to be minimized. Also, use of relatively high temperatures might be expected to complicate the process by increasing the solubility of the tetrabromobisphenol-A in the solvent solution and possibly necessitate a final cooling of, or addition of water to, the reaction mass to effect the desired high yield precipitation of tetrabromobisphenol-A. The processes of this invention, however, can be operated without excessive coproduction of methyl bromide or ethyl bromide, and there is no requirement for a cooling step to obtain sufficient tetrabromobisphenol-A precipitation.

Operation at relatively high temperatures can contribute to additional process economy and product purity enhancement. Process economy, in part, can be realized because even at higher reaction mass temperatures, cooling tower water can be used to cool the reactor instead of using refrigeration which is required by processes that are operated at low temperatures.

Typically temperatures are within the range of from about 30 to about 100° C., and preferably are in the range of about 50 to about 100° C. More highly preferred temperatures are within the range of from about 50 to about 80° C. These preferred temperatures in the range of about 50 to about 100° C. and in the range of about 50 to about 80° C. will be utilized during at least about 80%, and preferably, during at least 90% of the time the feeding of the bisphenol-A and/or underbrominated bisphenol-A to or with excess bromine is taking place, especially when conducting the process as a batch operation. More uniform temperatures within these ranges are typically maintained when operating the process on a continuous basis. However, programmed fluctuations in temperature within these ranges can be utilized in continuous operations, if desired. The most highly preferred temperatures are within the range of from about 50 to about 70° C. Temperatures below 30° C. can be used, but the organic solvent to bisphenol-A and/or underbrominated bisphenol-A weight ratio may well need to be high, say from 8:1 to 15:1. For these ratios, temperatures of 30 to 50° C. may be suitable.

The bromination of bisphenol-A and/or underbrominated bisphenol-A is an exothermic reaction as is the oxidation of HBr with $H_2O_2$. To control the reaction mass temperature, it may become necessary to remove heat from the reaction mass. Heat removal can be effected by running the reaction at reflux with the condenser facilitating the heat removal. If it is desired to operate at a temperature below the atmospheric boiling point of the reaction mixture, the reaction can be run under sub-atmospheric pressure.

Generally, the basic concepts of the processes of this invention are not appreciably affected by the process pressure. Thus, the process can be run under sub-atmospheric, atmospheric or super-atmospheric pressure.

At process initiation, it is desirable to charge the reactor with a liquid pre-reaction charge which will become a part of the reaction mass upon the commencement of the feed. The liquid charge will provide a stirable reaction mass and act as a heat sink to moderate temperature changes in the reaction mass. The liquid charge is preferably comprised of water and the same water-miscible organic solvent that is to be fed in the bisphenol-A and/or underbrominated bisphenol-A solution or slurry. It is preferred that the liquid charge be acidic, e.g., containing from 1 to 20 wt % acid such as $HBr_2$ HCl, or the like. The acid seems to promote good color in the initial tetrabromobisphenol-A produced. Further, it is preferred that the solvent be saturated with solvated tetrabromobisphenol-A. It is also preferred that the reactor be charged with seed particles of tetrabromobisphenol-A. The saturation of the solvent and the presence of the seed particles both act to enhance the precipitation of the tetrabromobisphenol-A produced during the bromination period. It is most practical to use a heel from a previously run process of this invention as the liquid charge. The tetrabromobisphenol-A seed particles can be brought over from the previous run or can be added separately. If a heel is not available, it is also possible to use a separate water and water-miscible organic solvent feed, which are a part of the total solution feed, to form the initial liquid charge. In this scheme, an initial amount of water and water-miscible organic solvent are fed to the reactor prior to the initiation of the solvated bisphenol-A portion and/or the slurry of underbrominated bisphenol-A portion of the solution or slurry feed. The only caveat to this scheme is that there must be apportionment of the various feeds making up the solution feed so that there will still be compliance with the various parameters which define the processes of this invention.

If the process of this invention is run as a batch process, the $Br_2$ and solution or slurry feeds are fed to a stirred reactor until they are exhausted. There is no need for a post-feed cook period of any significant length as, under the reaction conditions, the bromination of bisphenol-A and/or underbrominated bisphenol-A to tetrabromobisphenol-A occurs quite rapidly. Also, since the water content of the reaction mass is so large and since the tetrabromobisphenol-A is so insoluble in the presence of such an amount of water, there is only a modicum of benefit in cooling the final reaction mass. The benefit of cooling resides mainly in reducing the vapor pressure of solvated gaseous bromides, e.g., methyl bromide or ethyl bromide, in the reaction mass prior to the liquid-solids separation. There also may possibly be some reduction in rate in the formation of these alkyl bromides. In addition, depending upon the water content of the reaction mass, cooling may allow for additional precipitation of tetrabromobisphenol-A from the reaction mass. When operating within the preferred ranges recited herein, the additional precipitation benefit may not be worth the cost associated with obtaining same. Additionally, depending on the separation technique used, cooling the reaction mass may make it easier to handle downstream from the reactor. Thus, if none of the above are of concern or relative value, then the reaction mass can be subjected to liquid-solids separation as soon as it can be transported to the separation equipment. If, however, cooling is desired, the cooling time will depend upon how the reaction mass is to be cooled and to what temperature it is to be cooled. In a laboratory setting, cooling times can range from about one minute to about thirty minutes.

Additional time may also be used between the end of the co-feed and the precipitate recovery, if it is desired, to add additional water to the reaction mass at the end of the co-feed to insure that even more tetrabromobisphenol-A precipitate is formed in the reaction mass. The water addition and precipitation time can be very short, e.g., less than about thirty minutes.

Irrespective of whether or not the reaction mass is cooled or treated with more water, it is to be understood that the additional time used does not appreciably increase the total amount of tetrabromobisphenol-A produced by the process (the total amount includes that which is a precipitate and that which is solvated in the reaction mass). These additional times, therefore, are not to be considered cook times in the same way as are the cook times taught for use in prior art processes.

After the recovery of the solids from the liquid, the solids are preferably washed with a solution of water and the particular water-miscible organic solvent used in the reaction. The washing removes essentially all the mother liquor from the solids. The mother liquor typically contains impurities such as tribromophenol, $HBr_2$ and hydrolyzable impurities. A typical wash can be a 30 wt % methanol or ethanol in water solution. The washed solids are then rewashed with deionized water to remove any remaining water-miscible organic solvent from the first wash so as to minimize emission problems when drying the product.

When run in the continuous mode, the reactor is preferably a continuously stirred tank reactor. The reaction mass is being continuously formed and a portion thereof is being removed from the reactor during the reaction mass formation. The reactor design should be such that the average residence time in the reactor is sufficient to ensure tetrabromination of substantially all of the bisphenol-A and/or underbrominated bisphenol-A. Terms such as "continuous feed" and "continuous withdrawal" and terms of analogous import are not meant to exclude interrupted feeds or withdrawals. Generally, such interruptions are of short duration and may be suitable depending upon the scale and design of the reactor. For example, since the tetrabromobisphenol-A precipitate will tend to settle near the bottom of the reactor, a withdrawal may be made and then stopped for a period of time to allow for precipitate build-up to occur prior to the next withdrawal. Such a withdrawal is to be considered continuous in the sense that the withdrawal does not await the completion of the reactor feeds as is characteristic of batch processes.

Whether the continuous withdrawal is interrupted or not, the withdrawal results in a portion of the liquid and a portion of the solids in the reaction mass to be withdrawn together. The solids portion will be predominately tetrabromobisphenol-A. This mix can be filtered, the precipitate washed, etc., as is done for the above described batch mode case.

Experimental evidence available to date indicates that in the continuous mode of operation, the preferred reactor residence time should be within the range of from about 30 to about 150 minutes when using a stirred-tank reactor and the process conditions which are preferred for that operating mode. Reactor residence time, as used here, is the reactor volume divided by the flow rate at which slurry is removed from the reactor.

Product of excellent quality can be produced pursuant to this invention. The tetrabromobisphenol-A product can have a purity of 97 wt % and above, and with a very small tribromobisphenol-A content, if any, of about 2 wt %. Moreover, it is possible to produce tetrabromobisphenol-A product having an APHA color less than about 50 (as determined by dissolving 80 grams of tetrabromobisphenol-A product in 100 mL of acetone). Hydrolyzable bromides can also be kept low, generally below about 60 ppm. The process yields are impressive, with yields within the range of from about 95 to about 99% being possible.

As can be appreciated from the foregoing, the water content of the solvent, the reaction temperature, and the HBr and $Br_2$ contents in the reaction mass during the bisphenol-A and/or underbrominated bisphenol-A feed all contribute to obtaining the desired tetrabromobisphenol-A product in an efficient manner. The selection of particular values for each of these process parameters to obtain the results desired will depend on each practitioner's needs and upon the equipment available. One practitioner may emphasize one benefit of using a process of this invention over other possible benefits. Thus, that practitioner may select different process parameter values than those selected by another practitioner who desires to highlight other benefit(s).

The use of the oxidation of the co-generated HBr to produce a part of the $Br_2$ needs for the processes of this invention may possibly be attractive in a situation where the oxidation is more economical than the cost of providing for an equivalent amount of $Br_2$ in the feed to the reactor. However as noted above, one of the features of this invention, that of maintaining in the liquid phase of the reaction mass an amount of HBr that will protect the tetrabromobisphenol-A from adverse color development by the intentional or unintentional variance of the unreacted bromine concentration in the liquid phase to a concentration in the range of from above about 20,000 to about 80,000 ppm, should be taken into consideration in assessing whether or not to resort to such in situ bromine formation.

Though preferably designed to minimize the production of methyl bromide or ethyl bromide coproduct, the processes of this invention are readily adaptable to modification to coproduce methyl bromide or ethyl bromide.

While the foregoing descriptions of the oxidation of HBr generally speak of the HBr being oxidized in the reactor or reaction mass, it is within the scope of the processes of this invention to also remove HBr from the reactor and oxidize it outside of the reactor (i.e., in another suitable closed vessel or like apparatus) and then to send the so-produced $Br_2$ back to the reactor, or to separately generate bromine needed for the process by operation of a separate installation wherein HBr from one or more other sources is oxidized to bromine.

When feeding HBr to the reactor, such HBr can be either recycled HBr recovered from the off-gases of the bromination reaction, or non-indigenous HBr obtained from other sources, or a combination of both such sources.

It will be apparent from the foregoing description that in conducting the various processes of this invention it is important during at least a substantial portion of the time during which the reactants are being contacted with each other so that bromination is taking place, to provide for the presence in the liquid phase of the reaction mass of an amount of (i) unreacted bromine that is in excess over the stoichiometric amount theoretically required to convert the bisphenol-A and/or underbrominated bisphenol-A to tetrabromobisphenol-A, and (ii) HBr that will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm, so that a tetrabromobisphenol-A precipitate of little or no color is formed continuously during at least a substantial portion of such time. Since the process can be conducted as a batch process or as a continuous process, and since various ways and conditions of feeding and operating can be used, the term "substantial portion" is not an absolute invariable fractional number, but rather is to be understood with the application of common sense. Simply stated, to achieve the greatest benefits made possible by this invention one should, to the extent practicable under the particular set of operating parameters being used, arrange to reach the conditions specified in (i) and (ii) and concomitant continuous precipitate formation with as little delay as is feasible. And once those conditions have been reached they should be maintained as long as is practicable during the bromination. An advantage of a continuous mode of operation is that once the steady state of operation within these conditions has been reached, it is possible to maintain them as long as is desired. In such case reaction mass and precipitate formed during the start up phases of the operation prior to reaching the selected steady state conditions can be discarded.

The following Examples are presented to illustrate the practice of, and advantages made possible by, this invention. These Examples are not intended to limit, and should not be construed as limiting, the scope of this invention to the particular operations or conditions described therein.

The operations described in each of Examples 1–4 were conducted in a one-liter flask equipped with a mechanical stirrer, condenser, thermometer, and a down-drain to continually remove slurry from the reactor. The flask was fitted with a dip tube (⅛ inch O.D.) for feeding bromine vapor, and two feed tubes (⅛ O.D.) which terminated in the vapor phase, for feeding bisphenol-A solution and 50% $H_2O_2$ solution or deionized water. The top of the condenser was connected to a vacuum pump. The temperature of the reaction was maintained at 60 to 70° C. by controlling the vacuum at about 26 inches of Hg. Bisphenol-A (BPA) solution, bromine and H202 solution or water were fed to the reactor using uncalibrated peristaltic pumps. The bromine tube from the pump was connected to a nitrogen inlet and a bromine vaporizer (a flask heated with steam) and a gas outlet connected to the dip tube in the reactor. BPA solution was prepared by dissolving 4000 g of BPA in 4700 g of ethanol and 2000 g of water.

EXAMPLE 1

A 50 wt % solution (200 mL) of ethanol in water was charged to the reactor as the heel. BPA, $H_2O_2$ and bromine were fed to the reactor at flow rates of about 9.0 mL/min., about 0.9 mL/min., and about 1.8 mL/min., respectively. The bromine feed was kept stoichiometrically ahead of the BPA feed, and as a result the reaction mass remained pale yellow. The temperature of the reactor rose to about 60° C. and was kept at that temperature by reflux cooling. The product slurry was continually drained from the bottom of the reactor to keep a constant level in the reactor. After reaching the steady state, the slurry was filtered and washed with 30 wt % aqueous ethanol and then with deionized water. The washed precipitate was dried and analyzed. The product tetrabromobisphenol-A (TBBPA) had APHA color of 30 and purity of 98.3%. The mother liquor was found to contain 18.4% HBr and 0.7% $Br_2$. The ratio of HBr/$Br_2$ was 26.3.

EXAMPLE 2

The experiment was repeated again using flow rates of about 9.0 mL/min, about 0.9 mL/min, and about 1.8 mL/min as in Example 1. However, in this experiment no vacuum was employed, and instead of reflux cooling, the temperature was maintained at about 60° C. by external cooling of the reactor. After reaching steady state operation, the reaction was discontinued. The isolated product had APHA color of 30 and purity of 99.6%. The mother liquor contained 24.4% HBr and 1.6% $Br_2$. The ratio of $HBr/Br_2$ was 15.3.

EXAMPLE 3

In this experiment water was fed to the reactor in place of $H_2O_2$. BPA solution, water and bromine were fed to the reactor at flow rates of about 9.0 mL/min., about 0.9 mL/min., and about 2.7 mL/min. respectively. The temperature of the reactor was maintained at 60–70° C. by reflux cooling. The slurry was orange due to the presence of unreacted bromine in the reaction mixture. The product TBBPA isolated had APHA color of 50 and purity of 97.4%. The mother liquor had 42% HBr and 3.7% $Br_2$. The ratio of $HBr/Br_2$ was 11.4.

EXAMPLE 4

BPA solution, water and bromine were fed to the reactor at flow rates of about 9.0 mL/min., about 0.9 mL/min., and about 2.9 mL/min. The temperature of the reactor was maintained at 60–70° C. by reflux cooling. As there was significant amounts of unreacted bromine in the reaction mass, the slurry was dark orange. The product isolated had APHA color of 70 and purity of 99.0%. The mother liquor contained 49% HBr and 7.9% $Br_2$. The ratio of $HBr/Br_2$ was 6.2.

It is to be understood that the processes of this invention can be run in combination with processes having process parameters not of this invention. For example, if it is desired to produce an intermediate amount of methyl bromide ethyl bromide, a process similar to a process described above using methanol or ethanol as the water-miscible organic solvent but with process parameters which promote the formation of methyl bromide or ethyl bromide, such as, for example, use of a low water content in the vicinity of about 10 wt %. This process could be run for a period of time and then could be interrupted with the imposition of the parameters of this invention so as to diminish methyl bromide or ethyl bromide production. In this way, the methyl bromide or ethyl bromide production can be controlled within desired production limits by combining both processes.

As can be appreciated from the above results as summarized in the Table, and when viewed in their broadest aspects, the processes of this invention effect the high yield production of a highly pure tetrabromobisphenol-A product by providing a reaction system in which there is directly formed a tetrabromobisphenol-A precipitate at such speed that there is insufficient opportunity for the significant precipitation of the intermediate, tribromobisphenol-A, while at the same time not requiring the amount of excess unreacted bromine in the reaction mass to be closely controlled in order to prevent formation of highly colored tetrabromobisphenol-A product.

TABLE

| $HBr/Br_2$ ratio | Unreacted $Br_2$, wt % | APHA Color of Product | Product Purity, % |
|---|---|---|---|
| 26.3 | 0.7 | 30 | 98.3 |
| 15.3 | 1.6 | 30 | 99.6 |
| 11.4 | 3.7 | 50 | 97.4 |
| 6.2 | 7.9 | 70 | 99.0 |

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing tetrabromobisphenol-A which comprises:
    a) contacting, during a period of time, bromine and a continuous or substantially continuous feed of bisphenol-A and/or underbrominated bisphenol-A in a reaction mass having a temperature within the range of from about 30° C. to about 100° C. and having a liquid phase comprised of a water-miscible organic solvent and water, in which liquid phase, tetrabromobisphenol-A is relatively insoluble;
    b) during all or substantially all of said period of time, maintaining in the liquid phase of the reaction mass, an amount of HBr which will protect the color of the tetrabromobisphenol-A precipitate in d) from being adversely affected by the intentional or unintentional variance of the unreacted bromine concentration described in c) to above about 20,000 ppm and up to about 80,000 ppm;
    c) during all or substantially all of said period of time, having in the liquid phase of the reaction mass, a presence of from about 50 ppm to about 80,000 ppm unreacted bromine; and
    d) during all or substantially all of said period of time, precipitating tetrabromobisphenol-A from the reaction mass.

2. A process of claim 1 wherein the amount of HBr in the liquid phase of the reaction mass is, on a weight basis, from about 6 to about 50 times as much as the maximum amount of unreacted bromine that is expected to be in the liquid phase of the reaction mass during a).

3. A process of claim 1 wherein the tetrabromobisphenol-A precipitated in d) has a purity of at least about 95 wt % and is present in an amount giving at least about a 90% yield based upon the amount of bisphenol-A and/or underbrominated bisphenol-A fed.

4. A process of claim 1 wherein the tetrabromobisphenol-A-containing precipitate in d) has an APHA color of about 50 or less as determinable using a solution of 80 grams of the precipitate in 100 mL of acetone.

5. A process of claim 1 wherein the amount of HBr in the liquid phase of the reaction mass is, on a weight basis, from about 10 to about 20 times as much as the maximum amount of unreacted bromine that is expected to be in the liquid phase of the reaction mass during a).

6. A process of claim 1 wherein during at least a portion of said period of time, the liquid phase of the reaction mass has a presence of unreacted bromine above about 20,000 ppm but not above about 80,000 ppm.

7. A process of claim 1 wherein during at least a portion of said period of time, the liquid phase of the reaction mass has a presence of unreacted bromine above about 20,000 ppm but not above about 35,000 ppm.

8. A process of claim 1 wherein the bisphenol in the continuous or substantially continuous feed in a) is bisphenol-A.

9. A process of claim 1 wherein the bisphenol in the continuous or substantially continuous feed in a) is at least one underbrominated bisphenol-A species.

10. A process of claim 1 wherein the bisphenol in the continuous or substantially continuous feed in a) is bisphenol-A and underbrominated bisphenol-A.

11. A process of claim 1 wherein the process is conducted as a batch process.

12. A process of claim 1 wherein the process is conducted as a continuous process, and wherein said precipitate is removed from the reaction mass during the continuous or substantially continuous feed in a).

13. A process of claim 1 wherein said water-miscible organic solvent is a water-miscible alkanol.

14. A process of any of claims 1–12 wherein said water-miscible organic solvent is methanol or ethanol.

15. A process of claim 1 wherein said water-miscible organic solvent is a water-miscible alkanol; wherein the amount of HBr in the liquid phase of the reaction mass is, on a weight basis, from about 6 to about 50 times as much as the maximum amount of unreacted bromine that is expected to be in the liquid phase of the reaction mass during a); wherein the tetrabromobisphenol-A precipitated in d) has a purity of at least about 95 wt % and is present in an amount giving at least about a 90% yield based upon the amount of bisphenol-A and/or underbrominated bisphenol-A fed; and wherein the tetrabromobisphenol-A-containing precipitate in d) has an APHA color of about 100 or less as determinable using a solution of 80 grams of the precipitate in 100 mL of acetone.

16. A process of claim 15 wherein the process is conducted as a batch process; wherein the bisphenol in said continuous or substantially continuous feed in a) is bisphenol-A; wherein said alkanol is methanol or ethanol; and wherein the amount of HBr in the liquid phase of the reaction mass is, on a weight basis, from about 10 to about 20 times as much as the maximum amount of unreacted bromine that is expected to be in the liquid phase of the reaction mass during a).

17. A process of claim 15 wherein the process is conducted as a continuous process; wherein the bisphenol in said continuous or substantially continuous feed in a) is bisphenol-A; wherein said alkanol is methanol or ethanol; wherein the amount of HBr in the liquid phase of the reaction mass is, on a weight basis, from about 10 to about 20 times as much as the maximum amount of unreacted bromine that is expected to be in the liquid phase of the reaction mass during a); and wherein the precipitate is removed from the reaction mass during the continuous or substantially continuous feed in a).

18. A process of any of claims 15–17 wherein the alkanol is ethanol, and wherein said temperature is in the range of about 50 to about 80° C.

19. A process for the production of tetrabromobisphenol-A, which process comprises:
  a) feeding to a reactor at least bisphenol-A and/or underbrominated bisphenol-A, bromine, water, and a water-miscible organic solvent, to at least partially form a reaction mass having a liquid phase containing from above about 15 to about 85 wt % water, the wt % being based upon the amount of water and water-miscible organic solvent in the liquid phase; and
  b) during at least a substantial portion of a), (i) providing for the presence in the liquid phase of the reaction mass of an amount of unreacted bromine that is in excess over the stoichiometric amount theoretically required to convert the bisphenol-A and/or underbrominated bisphenol-A to tetrabromobisphenol-A, and to continuously form during substantially all of the time feeding in a) is occurring, a precipitate comprised mainly of tetrabromobisphenol-A, the yield of precipitated tetrabromobisphenol-A during substantially all of the time the feeding in a) is occurring being at least about 90% based on the amount of the bisphenol-A or underbrominated bisphenol-A or combination thereof fed up to that point in time, and (ii) providing for an amount of HBr in the liquid phase of the reaction mass which will protect the color of the tetrabromobisphenol-A precipitate from being adversely affected by the intentional or unintentional variance of the unreacted bromine concentration to a concentration in the range of from above about 20,000 ppm to about 80,000 ppm.

20. A process of claim 19 wherein at least a portion of the bisphenol-A or underbrominated bisphenol-A or combination thereof and of the water-miscible organic solvent is fed as a preformed solution, wherein the bromine is fed as a separate feed stream, and wherein HBr oxidant is also fed as a separate feed stream.

21. A process of claim 19 wherein the feeds to the reactor include at least (i) a preformed solution of bisphenol-A or underbrominated bisphenol-A or combination thereof, water, and water-miscible organic solvent, and (ii) a separate feed of bromine, and wherein the bromine is fed sub-surface to the liquid phase in the reactor.

22. A process of claim 19 wherein the water-miscible organic solvent is a water-miscible alcohol, carboxylic acid, nitrile, or ether which is not cleaved in the reaction mass.

23. A process of claim 19 wherein the water-miscible organic solvent is an alcohol containing up to 4 carbon atoms.

24. A process of claim 19 wherein the water-miscible organic solvent is methanol or ethanol.

25. A process of claim 19 wherein the reaction mass contains from about 30 to about 85 wt % water based on the amount of water and water-miscible organic solvent in the liquid phase of the reaction mass.

26. A process of claim 19 wherein the reaction mass contains from about 30 to about 70 wt % water based on the amount of water and water-miscible organic solvent in the liquid phase of the reaction mass.

27. A process of claim 19 wherein the weight ratio of organic solvent to bisphenol-A and/or underbrominated bisphenol-A fed is within the range of from about 1:1 to about 10:1.

28. A process of claim 19 wherein the weight ratio of organic solvent to bisphenol-A and/or underbrominated bisphenol-A fed is within the range of from about 3:1 to about 5:1.

29. A process of claim 19 wherein during at least a substantial portion of a) the reaction mass temperature is within the range of from about 50 to about 100° C.

30. A process of claim 19 wherein the bisphenol fed is bisphenol-A, wherein at least a portion of the bisphenol-A and of the water-miscible organic solvent is fed as a preformed solution, wherein the bromine is fed as a separate feed stream, wherein the water-miscible organic solvent is a water-miscible alcohol, carboxylic acid, nitrile, or ether which is not cleaved in the reaction mass, and wherein the reaction mass contains from about 30 to about 85 wt % water based on the amount of water and the water-miscible organic solvent in the liquid phase of the reaction mass.

31. A process of claim 19 wherein the feeds to the reactor include at least the following two feeds: (i) a preformed solution consisting essentially of bisphenol-A, water, and water-miscible organic solvent, and (ii) a separate feed of bromine, wherein the bromine is fed sub-surface to the liquid phase in the reactor, wherein the water-miscible organic solvent is methanol or ethanol, wherein the reaction mass contains from about 30 to about 70 wt % water based on the amount of water and the methanol or ethanol in the liquid phase of the reaction mass, and wherein the reaction mass temperature is within the range of from about 50 to about 80° C. during at least about 80 percent of the time the feeding in a) is taking place.

32. A process of claim 19 wherein during at least a portion of the time the feeding in a) is taking place, the liquid phase of the reaction mass has a presence of unreacted bromine above about 20,000 ppm but not above about 80,000 ppm.

33. A process of any of claims 19, 30 or 31 wherein the amount of HBr in the liquid phase of the reaction mass is, on a weight basis, from about 6 to about 50 times as much as the maximum amount of unreacted bromine that is expected to be in the liquid phase of the reaction mass during the feeding in a).

34. A process of any of claims 19, 30 or 31 wherein at least about 95 wt % of the precipitate is tetrabromobisphenol-A, and wherein the precipitate has an APHA color of about 100 or less as determinable using a solution of 80 grams of the precipitate in 100 mL of acetone.

35. A process of any of claims 19, 30 or 31 wherein the amount of HBr in the liquid phase of the reaction mass is, on a weight basis, from about 10 to about 20 times as much as the maximum amount of unreacted bromine that is expected to be in the liquid phase of the reaction mass during the feeding in a).

36. A process for the production of tetrabromobisphenol-A, which process comprises:
  a) co-feeding $Br_2$ and a solution comprised of bisphenol-A and/or underbrominated bisphenol-A, water and a water-miscible organic solvent to a reactor to at least partially form a reaction mass having a liquid phase and a solids phase, the liquid phase containing water in an amount of from above about 15 to about 85 wt % water, the wt % being based upon the amount of water and water-miscible organic solvent in the liquid phase, the solids phase comprising predominately a precipitate of tetrabromobisphenol-A;
  b) the reaction mass liquid phase containing during all or substantially all of the time the co-feeding in a) is taking place, an amount of unreacted bromine that is in excess over the stoichiometric amount theoretically required to convert the bisphenol-A and/or underbrominated bisphenol-A to tetrabromobisphenol-A, such that during substantially all of the time of said co-feeding in a), the tetrabromobisphenol-A is being produced in a yield of at least about 90% based on the amount of the bisphenol-A and/or underbrominated bisphenol-A already fed;
  c) the reaction mass liquid phase also containing during all or substantially all of the time the co-feeding in a) is taking place, an amount of HBr which will protect the color of the tetrabromobisphenol-A precipitate from being adversely affected by the intentional or unintentional variance of the unreacted bromine concentration to a concentration in the range of from above about 20,000 ppm to about 80,000 ppm; and
  d) periodically or continuously removing tetrabromobisphenol-A precipitate from the reactor along with a portion of the reaction mass so that the volume of the reaction mass in the reactor remains substantially constant.

37. A process of claim 36 wherein the water-miscible organic solvent in a) is a water-miscible alcohol, carboxylic acid, nitrile, or ether which is not cleaved in the reaction mass.

38. A process of claim 36 wherein the water-miscible organic solvent in a) is an alcohol containing up to 4 carbon atoms.

39. A process of claim 36 wherein the water-miscible organic solvent in a) is methanol or ethanol.

40. A process of claim 36 wherein the liquid phase in a) contains from about 30 to about 85 wt % water based on the amount of water and water-miscible organic solvent in the liquid phase of the reaction mass.

41. A process of claim 36 wherein the liquid phase in a) contains from about 30 to about 70 wt % water based on the amount of water and water-miscible organic solvent in the liquid phase of the reaction mass.

42. A process of claim 36 wherein the weight ratio of organic solvent to bisphenol-A and/or underbrominated bisphenol-A in the solution fed in a) is within the range of from about 1:1 to about 10:1.

43. A process of claim 36 wherein the weight ratio of organic solvent to bisphenol-A and/or underbrominated bisphenol-A in the solution fed in a) is within the range of from about 3:1 to about 5:1.

44. A process of claim 36 wherein the temperature of the liquid phase of the reaction mass is within the range of from about 50 to about 100° C.

45. A process of claim 36 wherein the bromine is fed sub-surface to the liquid phase in the reactor, wherein the water-miscible organic solvent is methanol or ethanol, wherein if said solvent is methanol the reaction mass contains from about 30 to about 55 wt % water based on the total weight of water and methanol in the liquid phase, and if said solvent is ethanol the reaction mass contains from about 40 to about 65 wt % water based on the total weight of water and ethanol in the liquid phase, and wherein the reaction mass temperature is within the range of from about 50 to about 100° C. during at least about 80 percent of the time the co-feeding is taking place.

46. A process of claim 36 or 45 wherein the amount of HBr in the liquid phase of the reaction mass is, on a weight basis, from about 6 to about 50 times as much as the maximum amount of unreacted bromine that is expected to be in the liquid phase of the reaction mass during the feeding in a).

47. A process of claim 36 or 45 wherein at least about 95 wt % of the precipitate is tetrabromobisphenol-A, and wherein the precipitate has an APHA color of about 100 or less as determinable using a solution of 80 grams of the precipitate in 100 mL of acetone.

48. A process of claim 36 or 45 wherein the amount of HBr in the liquid phase of the reaction mass is, on a weight basis, from about 10 to about 20 times as much as the maximum amount of unreacted bromine that is expected to be in the liquid phase of the reaction mass during a).

49. A process of claim 36 or 45 wherein during at least a portion of the time the co-feeding in a) is taking place, the liquid phase of the reaction mass has a presence of unreacted bromine above about 20,000 ppm but not above about 80,000 ppm.

50. A process for the production of tetrabromobisphenol-A product, which process comprises providing a liquid phase reaction system to which bisphenol-A and/or underbrominated bisphenol-A is/are being fed and in which there is being formed a tetrabromobisphenol-A precipitate by the bromination of bisphenol-A and/or underbrominated bisphenol-A with an excess of bromine over the stoichiometric amount theoretically required to produce tetrabromobisphenol-A, and in which there is present during all or substantially all of the time the bisphenol-A and/or underbrominated bisphenol-A is/are being fed, an amount of HBr which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm, the bromination being conducted at such rate that (i) there is insufficient opportunity for significant precipitation of tribromobisphenol-A to occur, and (ii) while the bisphenol-A and/or underbrominated bisphenol-A is/are being fed, tetrabromobisphenol-A is being produced substantially continuously in a yield of at least about 90% based on the amount of the bisphenol-A already fed, the total precipitate formed by the process comprising at least about 95 wt % tetrabromobisphenol-A having an APHA color of less than about 100, said APHA color being determinable by dissolving 80 grams of the tetrabromobisphenol-A product in 100 mL of acetone.

51. A process of claim 50 wherein the bromination is performed at a temperature within the range of from about 50 to about 80° C.

52. A process of claim 50 wherein the amount of HBr in the liquid phase of the reaction system is, on a weight basis, from about 6 to about 50 times as much as the maximum amount of unreacted bromine that is expected to be in said liquid phase during the time bisphenol-A and/or underbrominated bisphenol-A is/are being fed.

53. A process of claim 50 wherein during at least a portion of the time bisphenol-A and/or underbrominated bisphenol-A is/are being fed, the liquid phase of the reaction system has a presence of unreacted bromine above about 20,000 ppm but not above about 35,000 ppm.

54. A process of claim 50 wherein the amount of HBr in the liquid phase of the reaction system is, on a weight basis, from about 10 to about 20 times as much as the maximum amount of unreacted bromine that is expected to be in said liquid phase during the time bisphenol-A and/or underbrominated bisphenol-A is/are being fed.

55. A process for the production of tetrabromobisphenol-A, which process comprises:
  a) feeding to a reactor, bisphenol-A and/or underbrominated bisphenol-A, hydrogen bromide, an HBr oxidant, water, and a water-miscible organic solvent, to partially form a reaction mass having a liquid phase containing in the range of about 30 to about 85 wt % water, the wt % being based upon the amount of water and water-miscible organic solvent in the liquid phase; and
  b) proportioning the feeds in a) such that during at least a substantial portion of the time when both the feeding and the bromination of bisphenol-A and/or underbrominated bisphenol-A are occurring, there is present in the liquid phase of the reaction mass (i) an amount of unreacted bromine that is in excess over the stoichiometric amount theoretically required to convert the bisphenol-A to tetrabromobisphenol-A, and (ii) an amount of HBr which will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm, to continuously form during substantially all of the time when both the feeding and the bromination are occurring, a precipitate comprised mainly of tetrabromobisphenol-A, the yield of precipitated tetrabromobisphenol-A during substantially all of the time when both the feeding and the bromination are occurring being at least about 90% based on the amount of the bisphenol-A and/or underbrominated bisphenol-A fed up to that point in time.

56. A process of claim 55 wherein the hydrogen bromide is fed as aqueous $HBr_2$ wherein the HBr oxidant is aqueous hydrogen peroxide and the water-miscible organic solvent is an alcohol.

57. A process of claim 56 wherein the process is conducted on a continuous basis and wherein the feeds to the reactor comprise separate concurrent feeds of (i) aqueous $HBr_2$ (ii) aqueous hydrogen peroxide, and (iii) a preformed solution of bisphenol-A and/or underbrominated bisphenol-A, and water-miscible organic solvent.

58. A process of any of claims 55–57 wherein bromine is also fed to the reactor.

59. A process of any of claims 55–57 wherein the liquid phase of the reaction mass contains in the range of about 30 to about 70 wt % of water based on the weight of the water and water-miscible organic solvent, and wherein the amount of HBr in the liquid phase of the reaction mass is, on a weight basis, from about 6 to about 50 times as much as the maximum amount of unreacted bromine that is expected to be present in said liquid phase during the time the feeding and the bromination are both occurring.

60. A process for the production of tetrabromobisphenol-A, which process comprises:
  a) brominating bisphenol-A and/or underbrominated bisphenol-A by feeding bisphenol-A and/or underbrominated bisphenol-A to a reaction mass having a reaction mass temperature which is in the range of from about 30 to about 100° C., and having a liquid phase, which liquid phase contains (i) water and a solvent quantity of a water-miscible organic solvent, the water being present in an amount of from about 30 to about 85 wt %, based on the weight of the water and water-miscible organic solvent in the reaction mass, and (ii) 50 to 80,000 ppm of unreacted $Br_2$ so that a precipitate containing at least about 95 wt % of tetrabromobisphenol-A is being formed substantially continuously during the time said feeding is taking place; and
  b) during substantially all of the time said feeding is taking place, having in the liquid phase of the reaction mass an amount of HBr sufficient to protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm.

61. A process of claim 60 wherein during at least a substantial portion of the feeding in a), at least a portion of the precipitate is continuously being removed from the reaction mass.

62. A process of claim 60 wherein at least a portion of the unreacted $Br_2$ in the liquid phase in a) is provided by the oxidation of HBr to $Br_2$.

63. A process of claim 62 wherein said oxidation is effected in situ by introducing an oxidant into the reaction mass to cause oxidation therein of HBr to $Br_2$.

64. A process of claim 63 wherein said oxidant is hydrogen peroxide introduced into the reaction mass in a water-containing solution.

65. A process of claim 64 wherein during at least a substantial portion of the feeding in a), at least a portion of the precipitate is continuously being removed from the reaction mass.

66. A process of claim 60 wherein the amount of HBr in the liquid phase of the reaction mass is, on a weight basis, from about 6 to about 50 times as much as the maximum amount of unreacted bromine that is expected to be in said liquid phase during the time bisphenol-A and/or underbrominated bisphenol-A is/are being fed.

67. A process of claim 60 wherein during at least a portion of the time bisphenol-A and/or underbrominated bisphenol-A is/are being fed, the liquid phase of the reaction mass has a presence of unreacted bromine above about 20,000 ppm but not above about 80,000 ppm.

68. A process for the production of tetrabromobisphenol-A, which process comprises:
   a) brominating bisphenol-A and/or underbrominated bisphenol-A by feeding bisphenol-A and/or underbrominated bisphenol-A to a reaction mass having a reaction mass temperature which is in the range of from about 30 to about 100° C., and having a liquid phase, which liquid phase contains (i) water and a solvent quantity of a water-miscible organic solvent, the water being present in an amount of from about 30 to about 85 wt %, based on the weight of the water and water-miscible organic solvent in the reaction mass, and (ii) at least about 50 ppm but no more than about 80,000 ppm, of unreacted $Br_2$ to continuously produce during at least a substantial portion of the feeding in a), a precipitate enriched in tetrabromobisphenol-A, said tetrabromobisphenol-A being produced in a yield of at least about 90% based on the amount of bisphenol-A and/or underbrominated bisphenol-A fed to the reaction mass;
   b) during at least a substantial portion of the feeding in a), having in the liquid phase of the reaction mass an amount of HBr sufficient to protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm; and
   c) during at least a substantial portion of the feeding in a), continuously removing at least a portion of said precipitate from the reaction mass.

69. A process of claim 60 or 68 wherein in a) the bisphenol being fed to the reaction mass is bisphenol-A.

70. A process of claim 60 or 68 wherein in a) the bisphenol being fed to the reaction mass is (i) underbrominated bisphenol-A or (ii) bisphenol-A and underbrominated bisphenol-A.

71. A process of claims 60 or 68 wherein the water-miscible organic solvent is an alcohol having up to 4 carbon atoms, wherein the amount of water in the liquid phase of the reaction mass is in the range of about 30 to about 70 wt % based on the weight of the water and the water-miscible organic solvent in said liquid phase, wherein during the feeding in a), wherein the temperature of said liquid phase is in the range of from about 50 to about 100° C., and wherein during at least part of the time the feeding in a) is taking place, said liquid phase contains in the range of more than about 20,000 ppm but no more than about 80,000 ppm of unreacted $Br_2$.

72. A process of claim 60 or 68 wherein the water-miscible organic solvent is methanol or ethanol or a mixture thereof, wherein during the feeding in a), the reaction mass temperature is in the range of from about 50 to about 80° C., and wherein during at least part of the time the feeding in a) is taking place, said liquid phase contains in the range of more than about 20,000 ppm but no more than about 35,000 ppm of unreacted $Br_2$.

73. A process of claims 60 or 68 wherein in a) the bisphenol being fed to the reaction mass is bisphenol-A, wherein the reaction mass temperature in a) is in the range of from about 50 to about 80° C., wherein the water-miscible organic solvent is ethanol, wherein the amount of water in the liquid phase of the reaction mass is in the range of about 40 to about 65 wt % based on the weight of the water and ethanol in said liquid phase, wherein during at least part of the time the feeding in a) is taking place, said liquid phase contains in the range of more than about 20,000 ppm but no more than about 35,000 ppm of unreacted bromine, and wherein the amount of HBr in the liquid phase of the liquid phase reaction system is, on a weight basis, from about 10 to about 20 times as much as the maximum amount of unreacted bromine that is expected to be in said liquid phase during the time bisphenol-A is being fed.

74. A process for protecting tetrabromobisphenol-A against excessive color development during its production by bromination of bisphenol-A and/or underbrominated bisphenol-A by bromine, which process comprises:
   a) feeding bisphenol-A and/or underbrominated bisphenol-A to a reaction mass having during all or substantially all of the time said feeding is taking place, a liquid phase in which tetrabromobisphenol-A is relatively insoluble comprising water and a water-miscible organic solvent;
   b) during all or substantially all of the time the feeding in a) is taking place, having in said liquid phase at least about 50 ppm but not more than about 80,000 ppm of unreacted bromine and having the temperature in the liquid phase in the range of from about 30 to about 100° C.;
   c) during all or substantially all of the time the feeding in a) is taking place, having the water and said organic solvent proportioned in said liquid phase at a weight ratio within the range of from about 30:70 to about 85:15 that enables a precipitate containing tetrabromobisphenol-A to be formed substantially continuously during substantially the entire time said feeding is taking place, and in a substantially continuous yield of at least 90% based on the amount of bisphenol-A and/or underbrominated bisphenol-A already fed in accordance with a) up to that time; and
   d) during all or substantially all of the time the feeding in a) is taking place, maintaining the relative proportions of HBr and $Br_2$ in the liquid phase of the reaction mass such that there is present therein an amount of HBr relative to the amount of bromine that will protect the color of the tetrabromobisphenol-A precipitate from being adversely affected by the intentional or unintentional variance of the unreacted bromine concentration in the liquid phase to a concentration in the range of from above about 20,000 ppm to about 80,000 ppm.

75. A process of claim 74 wherein in a) the bisphenol being fed to the reaction mass is bisphenol-A, wherein the reaction mass temperature in a) is in the range of from about 50 to about 80° C., wherein the water-miscible organic solvent is ethanol, wherein the amount of water in the liquid phase of the reaction mass is in the range of about 40 to about 65 wt % based on the weight of the water and ethanol, wherein during at least part of the time the feeding in a) is taking place, said liquid phase contains in the range of more than about 20,000 ppm but no more than about 35,000 ppm of unreacted bromine, and wherein the amount of HBr in the liquid phase of the reaction mass is, on a weight basis, from about 6 to about 50 times as much as the maximum amount of unreacted bromine that is expected to be in said liquid phase during the time bisphenol-A is being fed.

* * * * *

UNITED STATES PATENT AND TRADEMARK OFFICE
CERTIFICATE OF CORRECTION

PATENT NO. : 6,218,584 B1
DATED : April 17, 2001
INVENTOR(S) : Thanikavelu Manimaran, Hassan Y. Elnagar, Richard A. Holub, Alvin E. Harkins, Jr. and Bonnie G. McKinnie It is certified that error appears in the above-identified patent and that said Letters Patent is hereby corrected as shown below:

Title page,
Item [63], Related U.S. Application Data,
1.    Continuation-in-part of 09/096,332 filed Jun. 11, 1998, which in turn if a continuation-in-part of 08/945,158, filed via PCT on Apr. 18, 1996 via PCT, which in turn is a continuation-in-part of 08/426,996, filed Apr. 24, 1995, now abandoned, and a continuation-in-part of 08/550,044, filed Oct. 30, 1995, now Pat. No. 5,723,690, issued Mar. 3, 1998, which in turn is a continuation of 08/426,997, filed Apr. 24, 1995, now Pat. No. 5,527,971, issued Jun. 18, 1996, and a continuation-in-part of 08/426,998, filed Apr. 24, 1995, now abandoned, which in turn is a continuation-in-part of 08/398,837, filed Mar. 6, 1995, now abandoned; and
2.    Continuation-in-part of 08/945,158, filed Apr. 18, 1996, which is a continuation-in-part of 08/426,996, filed Apr. 24, 1995, now abandoned, and a continuation-in-part of 08/550,044, filed Oct. 30, 1995, now Pat. No. 5,723,690, issued Mar. 3, 1998, which in turn is a continuation of 08/426,997, filed Apr. 24, 1995, now Pat. No. 5,527,971, issued Jun. 18, 1996; and a continuation-in-part of 08/426,998, filed Apr. 24, 1995, now abandoned, which in turn is a continuation-in-part of 08/398,837, filed Mar. 6, 1995, now abandoned.

Item [56], References Cited,
          U.S. PATENT DOCUMENTS,
add:    6,002,050    12/1999    McKinnie    568    726

FOREIGN PATENT DOCUMENTS,
correction:         2026280    1/1995    (USSR)

Item [57], ABSTRACT,
Line 7, should read -- ... bisphenol-A ... --.

UNITED STATES PATENT AND TRADEMARK OFFICE
CERTIFICATE OF CORRECTION

PATENT NO. : 6,218,584 B1
DATED : April 17, 2001
INVENTOR(S) : Thanikavelu Manimaran, Hassan Y. Elnagar, Richard A. Holub, Alvin E. Harkins, Jr. and Bonnie G. McKinnie It is certified that error appears in the above-identified patent and that said Letters Patent is hereby corrected as shown below:

Column 28,
Line 55, should read -- . . . nitrile . . . --.

Column 32,
Line 2, should read -- . . . HBr . . . --.
Line 8, should read -- HBr . . . --.

Signed and Sealed this

Twenty-seventh Day of November, 2001

Attest:

*Attesting Officer*

NICHOLAS P. GODICI
*Acting Director of the United States Patent and Trademark Office*